US005667780A

United States Patent [19]
Ho et al.

[11] Patent Number: 5,667,780
[45] Date of Patent: Sep. 16, 1997

[54] ANTIBODIES TO SMDF

[75] Inventors: Wei-Hsien Ho, Palo Alto; Phyllis L. Osheroff, Woodside, both of Calif.

[73] Assignee: Genentech, Inc., South San Francisco, Calif.

[21] Appl. No.: 428,926

[22] Filed: Apr. 25, 1995

Related U.S. Application Data

[62] Division of Ser. No. 339,517, Nov. 14, 1994.

[51] Int. Cl.$^6$ ................... C07K 16/18; A61K 39/395; C12N 5/12
[52] U.S. Cl. ................... 424/139.1; 530/388.23; 530/388.85; 530/389.2; 530/391.3; 530/387.9; 530/387.3
[58] Field of Search ................... 424/133.1, 139.1, 424/141.1, 145.1, 156.1; 435/240.27; 530/387.3, 387.9, 388.15, 388.24, 388.85, 391.3

[56] References Cited

U.S. PATENT DOCUMENTS 4,968,603  11/1990  Slamon et al.

FOREIGN PATENT DOCUMENTS

| | | |
|---|---|---|
| WO91/18921 | 12/1991 | WIPO |
| WO92/12174 | 7/1992 | WIPO |
| WO92/18627 | 10/1992 | WIPO |
| WO92/20798 | 11/1992 | WIPO |
| WO93/22339 | 11/1993 | WIPO |
| WO94/00140 | 1/1994 | WIPO |
| WO94/04560 | 3/1994 | WIPO |

OTHER PUBLICATIONS

Corfas et al., "Differential Expression of ARIA Isoforms in Rat Brain" *Neuron* 14:103–115 (Jan. 1995).

Dobashi et al., "Characterization of a neu/c–erbB–2 protein–specific activating factor" *Proc. Natl. Acad. Sci.* 88:8582–8596 (1991).

Ho, W., et al., "Sensory and Motor Neuron–derived Factor" *Journal of Biological Chemistry* 270(24):14523–14532 (Jun 16, 1995).

Huang et al., "Purification and Characterization of the neu/erb B2 Ligand–Growth Factor from Bovine Kidney" *Journal of Biological Chemistry* 267(16):11508–11512 (1992).

Peles et al., "Cell–type interaction of Neu differentiation factor (NDF/heregulin) with Neu/HER–2 suggests complex ligand–receptor relationships" *EMBO Journal* 12(3):961–971 (1993).

Peles et al., "Isolation of the Neu/HER–2 Stimulatory Ligand: A 44 Kd Glycoprotein That Induces Differentiation of Mammary Tumor Cells" *Cell* 69(1):205–216 (1992).

Pinkas–Kramarski et al., "Brain neurons and glial cells express Neu differentiation factor/heregulin: A survival factor for astrocytes" *Proc. Natl. Acad. Sci. USA* 91:9387–9391 (1994).

Plowman et al., "Heregulin induces tyrosine phosphorylation of HER4/p180erbB4" *Nature* 366:473–475 (Dec. 2,–1993).

Shah et al., "Glial growth factor restricts mammalian neural crest stem cells to a glial fate" *Cell* 77:349–360 (1994).

Tarakhovsky et al., "A 25 kDa polypeptide is the ligand for p185Neu and is secreted by activated macrophages" *Oncogene* 6(12):2187–2196 (1991).

Yarden, "Biochemical Analysis of the Ligand for the neu Oncogenic Receptor" *Biochemistry* 30:3543–3550 (1991).

Benveniste, E.N. et al., "Purification and characterization of a human T–lymphocyte–derived glial growth–promoting factor" *Proc. Natl. Acad. Sci.* 82:3930–3934 (1985).

Brockes et al., "Glial growth factor–like activity in Schwann Cell tumors" *Annals of Neurology* 20(3):317–322 (1986).

Brockes et al., "Purification and preliminary characterization of a glial growth factor from the bovine pituitary" *Journal of Biological Chemistry* 255(18):8374–8377 (1980).

Brockes, J., "Assay and isolation of glial growth factor from the bovine pituitary" *Methods in Enzymoloty* 147:217–225 (1987).

Carraway et al., "The erbB3 gene product is a receptor for heregulin" *Journal of Biological Chemistry* 269(19):14303–14306 (1994).

Cohen, J.A. et al., "Expression of the neu proto–oncogene by Schwann Cells during peripheral nerve development and Wallerfan degeneration" *J. Neuroscience Res.* 31:622–634 (1992).

Corfas & Fischbach, "The number of Na$^+$ channels in cultured chick muscle is increased by ARIA, an acetylcholine receptor–inducing activity" *J. Neuroscience* 13(5):2118–2125 (1993).

Danilenko et al., "Neu differentiation factor (NDF) accelerates epidermal migration and differentiation in excisional wounds" *FASEB* 8((4–5)):abst no. 3101, p A535 (1994).

Davis & Stroobant, "Platelet–derived growth factors and fibroblast growth factors are mitogens for rat Schwann Cells" *Journal of Cell Biology* 110:1353–1360 (1990).

Davis, JG et al., "Isolation and characterization of a neu protein–specific activating factor from human ATL–2 cell conditioned medium" *Biochem. & Biophys. Res. Comm.* 179(3):1536–1542 (Sep. 30, 1991).

(List continued on next page.)

*Primary Examiner*—Lila Feisee
*Assistant Examiner*—Nancy A. Johnson
*Attorney, Agent, or Firm*—Wendy M. Lee

[57] ABSTRACT

Isolated SMDF, isolated DNA encoding SMDF, and antibodies to SMDF are disclosed. SMDF contains a β-type EGF-like domain and a N-terminal sequence which is distinct from all neuregulins reported so far. SMDF, when expressed in recombinant cell culture, activates tyrosine phosphorylation of the HER2/neu receptor in human breast cancer cells and displays mitogenic activity on Schwann cells. Northern blot and in situ hybridization analysis show that SMDF differs from other neuregulins in that it is nervous tissue specific, and is very highly expressed, in comparison to other neuregulins, in the human and rat spinal cord motor neurons and sensory neurons.

12 Claims, 4 Drawing Sheets

OTHER PUBLICATIONS

De Corte et al., "A 50 kDa protein present in conditioned medium of COLO–16 cells stimulates cell spreading and motility, and activates tyrosine phosphorylation of Neu/HER–2, in human SK–BR–3 mammary cancer cells" *J. Cell Science* 107:405–416 (1994).

Falls et al., "ARIA, a protein that stimulates acetylcholine receptor synthesis, is a member of the Neu ligand family" *Cell* 72:801–815 (1993).

Hoffman, Michelle, "New Clue Found to Oncogene's Role in Breast Cancer" *Science* 256:1129 (1992).

Holmes et al., "Identification of heregulin, a specific activator of p185$^{erb2}$" *Science* 256:1205–1210 1992).

Kuo et al., "Isolation and characterization of chick and human nARIA, a novel member of the ERBB2/HER ligand family which lacks the immunoglobulin domain" *Soc. Neuroscience Abst.* 20:abst.452.18, p 1095 1994).

Lemke & Brockes, "Identification and purification of glial growth factor" *J. Neurosci.* 4(1):75–83 (1984).

Levi et al., "The functional characteristics of Schwann Cells cultured from human peripheral nerve after transplantation into a gap within the rat sciatic nerve" *J. Neuroscience* 14(3):1309–1319 (1994).

Lupu et al., "Direct interaction of a ligand for the erbB2 oncogene product with the EGF receptor and p185$^{erbB2}$" *Science* 249:1552–1555 (1990).

Lupu et al., "Purification and Characterization of a Novel Growth Factor from Human Breast Cancer Cells" *Biochemistry* 31(32):7330–7340 (Aug. 1992).

Lupu et al., "Purification of a novel growth factor that binds exclusively to the erbB–2 receptor protein and induces cellular responses" *Proc. Am. Assoc. Cancer Res.* 32:abst. no. 297, p. 50 (1991).

Marchionni et al., "Glial growth factors are alternatively spliced erbB2 ligands expressed in the nervous system" *Nature* 362:312–318 (1993).

Meyer & Birchmeier, "Distinct isoforms of neuregulin are expressed in mesenchymal and neuronal cells during mouse development" *Proc. Natl. Acad. Sci.* 91:1064–1068 (1994).

Nagata et al., "Solution structure of the epidermal growth factor–like domain of heregulin–α, a ligand for p180$^{erbB-4}$" *EMBO J*, 13(15):3517–3523 (1994).

Orr–Urtreger et al., "Neural expression and chromosomal mapping of Neu differentiation factor to 8p12–p21" *Proc. Natl. Acad. Sci.* 90:1867–1871 (1993).

Peles & Yarden, "Neu and its Ligands: From an Oncogene to Neural Factors" *BioEssary* 15(12):815–824 (1993).

Samanta et al., "Ligand and p185$^{c-neu}$ density govern receptor interactions and tyrosine kinase activation" *Proc. Natl. Acad. Sci.* 91:1711–1715 (1994).

Sklar et al., "A novel growth factor for muscle–rhGGF2" *J. Cell Blochem.* abst:450, abst. W462 (1994).

Sliwkowski et al., "Coexpression of erbB2 and erbB3 proteins reconstitutes a high affinity receptor for heregulin" *Journal of Biological Chemistry* 269(20):14661–14665 (1994).

Wen et al., "Neu differentiation factor: a transmembrane glycoprotein containing an EGF Domain and an Immunoglobulin Homology Unit" *Cell* 69(3):559–572 (May 1, 1992).

Wen et al., "Structural and functional aspects of the multiplicity of neu differentiation factors" *Molecular & Cellular Biology* 14(3):1909–1919 (1994).

Yang et al., "Identification of different ARIA splice variants expressed by chick CNS and PNS neurons during development" *Soc. Neuroscience Abst.* 20:abst. no 452.17, p. 1095 (1994).

```
  1 GAATTCGGGACAGCCTCTCCTGCCGCCGCTGCTGCTGCCGCCGCCGCCACCGCCGGCTGGTCCTCCTTCTGCTTT

76 TACTTCTCCTGCATGACAGTTGTTTTCTTCATCTGAGCAGACACCAGCTTCAGATGCTCGAGGTGAGAAACATGC

151 CTTTCAGTTTGGGCTACTGGTTTACTTAATTAATCAGCCGGCAGCTCCGTCGATCTATTTTCGTCCCTGTCCTCT

226 TGACGAGCCCGGGATGGTTTGGAGTAGCATTTAAAAGAACTAGAAAAGTGGCCCAGAAACAGCAGCTTAAAGAAT

301 TATTACGATATACTTTGATTTTGTAGTTGCTAGGAGCTTTTCTTCCCCCCTTGCATCTTTCTGAACTCTTCTTGA

376 TTTTAATAATGGCCTTGGACTTGGACGATTTATCGATTTCCCCCTGTAAGATGCTGTATCATTTGGTTGGGGGGG

451 CCTCTGCGTGGTAATGGACCGTGAGAGCGGCCAGGCCTTCTTCTGGAGGTGAGCCGATGGAGATTTATTCCCCAG
  1                                                          M  E  I  Y  S  P  D

526 ACATGTCTGAGGTCGCCGCCGAGAGGTCCTCCAGCCCCTCCACTCAGCTGAGTGCAGACCCATCTCTTGATGGGC
  8  M  S  E  V  A  A  E  R  S  S  S  P  S  T  Q  L  S  A  D  P  S  L  D  G  L

601 TTCCGGCAGCAGAAGACATGCCAGAGCCCCAGACTGAAGATGGGAGAACCCCTGGACTCGTGGGCCTGGCCGTGC
 33  P  A  A  E  D  M  P  E  P  Q  T  E  D  G  R  T  P  G  L  V  G  L  A  V  P

676 CCTGCTGTGCGTGCCTAGAAGCTGAGCGCCTGAGAGGTTGCCTCAACTCAGAGAAAATCTGCATTGTCCCCATCC
 58  [C][C] A [C] L  E  A  E  R  L  R  G [C] L  N  S  E  K  I [C] I  V  P  I  L

751 TGGCTTGCCTGGTCAGCCTCTGCCTCTGCATCGCCGGCCTCAAGTGGGTATTTGTGGACAAGATCTTTGAATATG
 83  A [C] L  V  S  L [C] L [C] I  A  G  L  K  W  V  F  V  D  K  I  F  E  Y  D

826 ACTCTCCTACTCACCTTGACCCTGGGGGGTTAGGCCAGGACCCTATTATTTCTCTGGACGCAACTGCTGCCTCAG
108  S  P  T  H  L  D  P  G  G  L  G  Q  D  P  I  I  S  L  D  A  T  A  A  S  A

901 CTGTGTGGGTGTCGTCTGAGGCATACACTTCACCTGTCTCTAGGGCTCAATCTGAAAGTGAGGTTCAAGTTACAG
133  V  W  V  S  S  E  A  Y  T  S  P  V  S  R  A  Q  S  E  S  E  V  Q  V  T  V

976 TGCAAGGTGACAAGGCTGTTGTCTCCTTTGAACCATCAGCGGCACCGACACCGAAGAATCGTATTTTTGCCTTTT
158  Q  G  D  K  A  V  V  S  F  E  P  S  A  A  P  T  P  K  N  R  I  F  A  F  S

1051 CTTTCTTGCCGTCCACTGCGCCATCCTTCCCTTCACCCACCCGGAACCCTGAGGTGAGAACGCCCAAGTCAGCAA
183  F  L  P  S  T  A  P  S  F  P  S  P  T  R  N  P  E  V  R  T  P  K  S  A  T

1126 CTCAGCCACAAACAACAGAAACTAATCTCCAAACTGCTCCTAAACTTTCTACATCTACATCCACCACTGGGACAA
208  Q  P  Q  T  T  E  T  N  L  Q  T  A  P  K  L  S  T  S  T  S  T  T  G  T  S

1201 GCCATCTTGTAAAATGTGCGGAGAAGGAGAAAACTTTCTGTGTGAATGGAGGGGAGTGCTTCATGGTGAAAGACC
233  H  L  V  K [C] A  E  K  E  K  T  F [C] V  N  G  G  E [C] F  M  V  K  D  L

1276 TTTCAAACCCCTCGAGATACTTGTGCAAGTGCCCAAATGAGTTTACTGGTGATCGCTGCCAAAACTACGTAATGG
258  S  N  P  S  R  Y  L [C] K [C] P  N  E  F  T  G  D  R [C] Q  N  Y  V  M  A

1351 CCAGCTTCTACAGTACGTCCACTCCCTTTCTGTCTCTGCCTGAATAGGAGCATGCTCAGTTGGTGCTGCTTTCTT
283  S  F  Y  S  T  S  T  P  F  L  S  L  P  E  O

1426 GTTGCTGCATCTCCCCTCAGATTCCACCTAGAGCTAGATGTGTCTTACCAGATCTAATATTGACTGCCTCTGCCT

1501 GTCGCATGAGAACATTAACAAAAGCAATTGTATTACTTCCTCTGTTCGCGACTAGTTGGCTCTGAGATACTAATA

1576 GGTGTGTGAGGCTCCGGATGTTTCTGGAATTGATATTGAATGATGTGATACAAATTGATAGTCAATATCAAGCAG

1651 TGAAATATGATAATAAAGGCATTTCAAAGTCTCACTTTTATTGATAAAATAAAAATCATTCTACTGAACAGTCCA

1726 TCTTCTTTATACAATGACCACATCCTGAAAAGGGTGTTGCTAAGCTGTAACCGATATGCACTTGAAATGATGGTA

1801 AGTTAATTTTGATTCAGAATGTGTTATTTGTCACAAATAAACATAATAAAAGGAAAAAAAAAAACCCGAATTC
```

EGF
                    -like

FIG. 1A

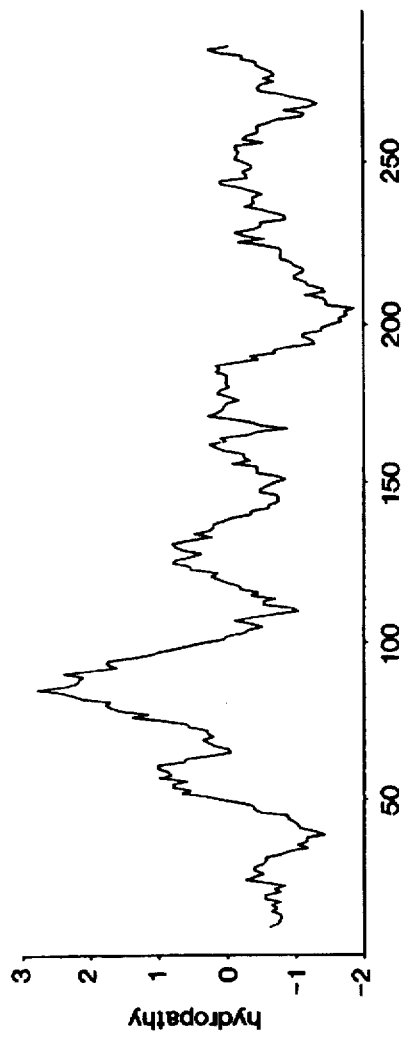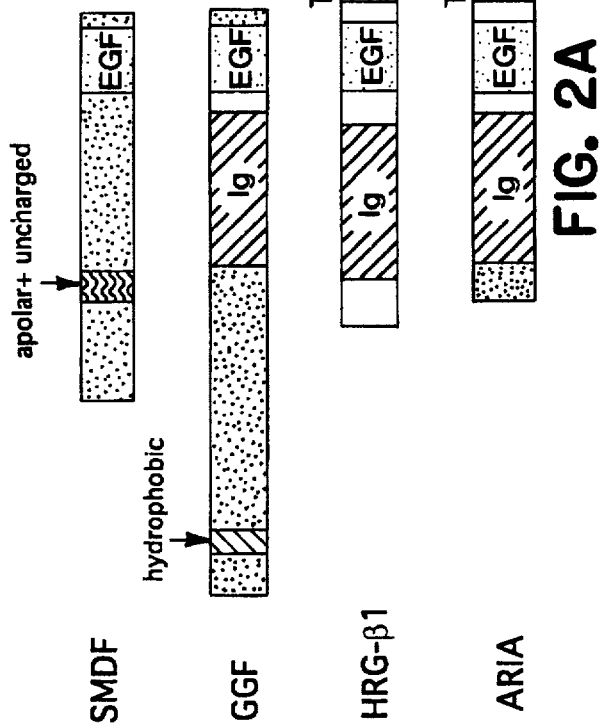
FIG. 1B
FIG. 2A

FIG. 2B-1

Ig-like domain / EGF-like domain

```
GGF     1    MRWRRAPRRSGRPGPRAQRPGSAARSSPPLPLLPLLLLGTAALAPGAAAGNEAAPAGASVCYSSPPSVGSV
GGF    73    QELAQRAAVVIEGKVHPQRRQQGALDRKAAAAGEAGAWGGDREPPAAGPRALGPPAEEPLLAANGTVPSWPTAP
SMDF    1                        MEIYSPDMSEVAAERSSSPSTQLSADPSLDGLPAAEDMPEPQTEDGRTPGLVGLAVPCCAC
GGF   148    VPSAGEPGEEAPYLVKVHQVWAVKAGGLKKDSLLTVRLGTWGHPAFPSCGRLKEDSRYIFFMEPDANSTSRAPAA
HRG-β1  1                                                                      MSERKEG

SMDF   62    LEAERLRGCLNSEKICIVPILACLVSLCLCIAGLKWVFVDKIFEYDSPTHLDPGGLGQDPIISLDATAASAVWVS
GGF   223    FRASFPPLETGRNLKKEVSRVLCKRCA PPQLKEMKSQESAAGSKLVLRCETSSEYSSLRFKWFKNGNELNRKNK
HRG-β1  8    RGKGKGKKKERGSGKKPESAAGSQSPA PPQLKEMKSQESAAGSKLVLRCETSSEYSSLRFKWFKNGNELNRKNK
ARIA    1                        MWATSEGPLQYSLAPTQTDVNSSYNT VPPKLKEMKNQEVAVGQKLVLRCETTSEYPALRFKWLKNGKEITKKNR
                                                                 **    ***        *

SMDF  137    SEAYTSPVSRAQSESEVQVTVQGDKAVVSFEPSAAPTPKNRIFAFSFLPSTAPSFPSPTRNPEVRTPKSATQPQT
GGF   298    PQNIKIQKKPGK-SELRINKASLADSGEYMCKVISKLGNDSASANITIVESN
HRG-β1 83    PQNIKIQKKPGK-SELRINKASLADSGEYMCKVISKLGNDSASANITIVESN EIITGMPASTEGAYVSSESPIRI
ARIA   75    PENVKIPKKQKKYSELHIYRATLADAGEYMCRVSSKLGNDSTKASVIITDTN
                     *     ***            *           ** ***  ***

SMDF  212    TETNLQTAPKLSTSTTGTSHLVKCAEKEKTFCVNGGECFMVKDLSNPSRYLCKCPNEFTGDRCQNYVMASFYK
GGF   349    -------ATSTSTTGTSHLVKCAEKEKTFCVNGGECFMVKDLSNPSRYLCKCPNEFTGDRCQNYVMASFYK
HRG-β1 157   SVSTEGANTSSSTSTSTTGTSHLVKCAEKEKTFCVNGGECFMVKDLSNPSRYLCKCPNEFTGDRCQNYVMASFYK
ARIA  127    -------ATSTSTTGTSHLTKCDIKQKAFCVNGGECYMVKDLPNPPRYLCKCPNEFTGDRCQNYVMASFYK
                                *  *  *      *                     **
```

```
SMDF      287  TSTPFLSLPE
GGF       413  TSTPFLSLPE

HRG-β1    232  HLGIEFMEAEELYQKRVLTITGICIALLVVGIMCVVAYCKTKKQRKKLHDRLRQSLRSERNNMMNIANGPHHPNP
ARIA      191  HLGIEFMEAEELYQKRVLTITGICIALLVVGIMCVVAYCKTKKQRKKLHDRLRQSLRSERNVMNMANGPHHPNP
                                 └─────────────────────────┘
                                         TM domain HRG-β1    307  PPENVQLVNQYVSKNVISSEHIVEREAETSFSTSHYTSTAHHSTTVTQTPSHSWSNGHTESILSESHSVIVMSSV
ARIA      266  PPDNVQLVNQYVSKNIISSERVVERETETSFSTSHYTSTTHHSMTVTQTPSHSWSNGHTESILSESHSVLVSSSV HRG-β1    382  ENSRHSSPTGGPRGRLNGTGGPRECNSFLRHARETPDSYRDSPHSERYVSAMTTPARMSPVDFHTPSSPKSPPSE
ARIA      341  ENSRHTSPTG-PRGRLNGIGGPREGNSFLRHARETPDSYRDSPHSERYVSAMTTPARMSPVDFHTPTSPKSPPSE HRG-β1    457  MSPPVSSMTVSMPSMAVSPFMEEERPLLLVTPPRLREKKFDHHPQQFSSFHHNPAHDSNSLPASPLRIVEDEEYE
ARIA      415  MSPPVSSLTISIPSVAVSPFMDEERPLLLVTPPRLREK-YDNHLQQFNSFHNNPTHESNSLPPSPLRIVEDEEYE HRG-β1    532  TTQEYEPAQEPVKKLANSRRAKRTKPNGHIANRLEVDSNTSSQSSNSESETEDERVGEDTPFLGIQNPLAASLEA
ARIA      489  TTQEYEPAQEPPKKLTNSRRVKRTKPNGHISSRVEVDSDTSSQSTSSESETEDERIGEDTPFLSIQNPMATSLEP HRG-β1    607  TPAFRLADSRTNPAGRFSTQEEIQARLSSVIANQDPIAV
ARIA      563  AAAYRLAENRTNPANRFSTPEELQARLSSVIANQDPIAV
```

FIG. 2B-2

ANTIBODIES TO SMDF

CROSS REFERENCE

This application is a divisional of co-pending U.S. application Ser. No. 08/339,517 filed 14 Nov. 1994, which application is incorporated herein by reference and to which application priority is claimed under 35 USC §120.

FIELD OF THE INVENTION

This application relates to sensory and motor neuron derived factor (SMDF), methods of making SMDF, and diagnostic and therapeutic uses thereof.

BACKGROUND OF THE INVENTION (i) erbB Proto-oncogenes

Transduction of signals that regulate cell growth and differentiation is regulated in part by phosphorylation of various cellular proteins. Protein tyrosine kinases are enzymes that catalyze this process. Receptor protein tyrosine kinases are believed to direct cellular growth via ligand-stimulated tyrosine phosphorylation of intracellular substrates. Growth factor receptor protein tyrosine kinases of the class I subfamily include the 170 kDa epidermal growth factor receptor (EGFR) encoded by the erbB gene. erbB has been causally implicated in human malignancy. In particular, increased expression of this gene has been observed in more aggressive carcinomas of the breast, bladder, lung and stomach. See Neal et al., *Lancet*, 1:366–368 (1985); Sainsbury et al., *Lancet*, 1:1389–1402 (1987); Yasui et al., *Int. J. Cancer*, 41: 211–217 (1988); and Veale et al., *Cancer*, 55:513–516 (1987).

The second member of the class I subfamily, $p185^{neu}$, was originally identified as the product of the transforming gene from neuroblastomas of chemically treated rats. The neu gene (also called erbB2 and HER2) encodes a 185 kDa receptor protein tyrosine kinase. Amplification and/or overexpression of the human HER2 gene correlates with a poor prognosis in breast and ovarian cancers (Slamon et al., *Science*, 235:177–182 [1987]; and Slamon et al., *Science*, 244:707–712 [1989]). Overexpression of HER2 has also been correlated with other carcinomas including carcinomas of the stomach, endometrium, salivary gland, lung, kidney, colon and bladder. See, among others, King et al., *Science*, 229:974 (1985); Yokota et al., *Lancet*: 1:765–767 (1986); Fukushigi et al., *Mol Cell Biol.*, 6:955–958 (1986); Slamon et al. (1987), supra; Geurin et al., *Oncogene Res.*, 3:21–31 (1988); Cohen et al., *Oncogene*, 4: 81–88 (1989); Yonemura et al., *Cancer Res.*, 51:1034 (1991); Borst et al., *Gynecol, Oncol.*, 38:364 (1990); Weiner et al., *Cancer Res.*, 50:421–425 (1990); Kern et al., *Cancer Res.*, 50:5184 (1990); Park et al., *Cancer Res.*, 49:6605 (1989); Zhau et al., *Mol. Carcinog.*, 3:354–357 (1990); and McCann et al., *Cancer*, 65: 88–92 (1990). Accordingly, Slamon et al. in U.S. Pat. No. 4,968,603 describe and claim various diagnostic assays for determining HER2 gene amplification or expression in tumor cells. Slamon et al. discovered that the presence of multiple gene copies of HER2 oncogene in tumor cells indicates that the disease is more likely to spread beyond the primary tumor site, and that the disease may therefore require more aggressive treatment than might otherwise be indicated by other diagnostic factors. Slamon et al. conclude that the HER2 gene amplification test, together with the determination of lymph node status, provides greatly improved prognostic utility.

Expression of the HER2 gene in non-cancerous tissue has also been investigated. For example, Cohen et al. found that the HER2 gene is expressed by Schwann cells during peripheral nerve development and wallerian degeneration. Accordingly, they concluded that $p185^{HER2}$ plays a role in regulation of proliferation or differentiation of Schwann cells. Cohen et al., *J. Neuroscience Res.*, 31:622–634 (1992).

A further related gene, called erbB3 or HER3, has also been described. See U.S. Pat. No. 5,183,884; Kraus et al., *PNAS, U.S.A.*, 86: 9193–9197 (1989); EP Pat Appln No 444,961A1; and Kraus et al., *PNAS, U.S.A.*, 90:2900–2904 (1993). Kraus et al. (1989) discovered that markedly elevated levels of erbB3 mRNA were present in certain human mammary tumor cell lines indicating that erbB3, like erbB and erbB2, may play a role in some human malignancies. Also, Kraus et al. (1993) showed that EGF-dependent activation of the erbB3 catalytic domain of a chimeric EGFR/erbB3 receptor resulted in a proliferative response in transfected NIH-3T3 cells. Furthermore, these researchers demonstrated that some human mammary tumor cell lines display a significant elevation of steady-state erbB3 tyrosine phosphorylation further indicating that this receptor may play a role in human malignancies. Accordingly, diagnostic bioassays utilizing nucleic acid encoding erbB3 are described by Kraus et al. in U.S. Pat. No. 5,183,884.

Recently, the class I subfamily of growth factor receptor protein tyrosine kinases was extended to include the HER4/$p180^{erbB4}$ receptor. See EP Pat Appln No 599,274; Plowman et al., *PNAS, U.S.A.*, 90:1746–1750 (1993); and Plowman et al., *Nature*, 366:473–475 (1993). Plowman et al. found that increased HER4 expression closely correlated with certain carcinomas of epithelial origin, including breast adenocarcinomas. Accordingly, diagnostic methods for detection of human neoplastic conditions (especially breast cancers) which evaluate HER4 expression are described in EP Pat Appln No. 599,274.

(ii) Neuregulins

The quest for the activator of the HER2 oncogene has lead to the discovery of a family of polypeptides collectively called "neuregulins". These proteins appear to result from alternative splicing of a single gene which was mapped to the short arm of human chromosome 8 by Orr-Urtreger et al., *PNAS, U.S.A.*, 90:1867–1871 (1993).

Holmes et al. isolated and cloned a family of polypeptide activators for the HER2 receptor which they termed heregulin-α (HRG-α), heregulin-β1 (HRG-β1), heregulin-β2 (HRG-β2), heregulin-β2-like (HRG-β2-like), and heregulin-β3 (HRG-β3). See Holmes et al., *Science*, 256:1205–1210 (1992); and WO 92/20798 as well as Hoffman et al., *Science*, 256:1129 (1992). The 45 kDa polypeptide, HRG-α, was purified from the conditioned medium of the MDA-MB-231 human breast cancer cell line. These researchers demonstrated the ability of the purified heregulin polypeptides to activate tyrosine phosphorylation of the HER2 receptor in MCF-7 breast tumor cells. Furthermore, the mitogenic activity of the heregulin polypeptides on SK-BR-3 cells (which express high levels of the HER2 receptor) was illustrated. Like other growth factors which belong to the EGF family, soluble HRG polypeptides appear to be derived from a membrane bound precursor (called pro-HRG) which is proteolytically processed to release the 45 kDa soluble form. These pro-HRGs lack a N-terminal signal peptide.

While heregulins are substantially identical in the first 213 amino acid residues, they are classified into two major types, α and β, based on two variant EGF-like domains which differ in their C-terminal portions. Nevertheless, these EGF-like domains are identical in the spacing of six cysteine residues contained therein. Nagata et al. describe the solution structure of the EGF-like domain of HRG-α in *EMBO. J.*, 13(15):3517–3523 (1994). Based on an amino acid sequence comparison, Holmes et al. found that between the first and sixth cysteines in the EGF-like domain, HRGs were 45% similar to heparin-binding EGF-like growth factor (HB-EGF), 35% identical to amphiregulin (AR), 32% identical to TGF-α, and 27% identical to EGF.

The 44 kDa neu differentiation factor (NDF), which is the rat equivalent of human HRG, was first described by Peles et al., *Cell*, 69:205–216 (1992); and Wen et al., *Cell*, 69:559–572 (1992). Like the HRG polypeptides, NDF has an immunoglobulin (Ig) homology domain followed by an EGF-like domain and lacks a N-terminal signal peptide. Subsequently, Wen et al., *Mol. Cell. Biol.*, 14(3):1909–1919 (1994) carried out "exhaustive cloning" to extend the family of NDFs. This work revealed six distinct fibroblastic pro-NDFs. Adopting the nomenclature of Holmes et al., the NDFs are classified as either α or β polypeptides based on the sequences of the EGF-like domains. Isoforms 1 to 4 are characterized on the basis of the variable justamembrane stretch (between the EGF-like domain and transmembrane domain). Also, isoforms a, b and c are described which have variable length cytoplasmic domains. These researchers conclude that different NDF isoforms are generated by alternative splicing and perform distinct tissue-specific functions. See also EP 505 148; and WO 93/22424 concerning NDF. NDF expression has been studied. In particular, Orr-Urtreger *PNAS, U.S.A.*, 90:1867–1871 (1993), using a mouse NDF probe which includes a partial Ig-like domain, found that NDF expression in mouse embryos was in the central and peripheral nervous system [including neuroepithelium that lines the lateral ventricles of the brain, dorsal root ganglia and ventral horn of the spinal cord (albeit weak) as well as intestine, stomach and adrenal cortex].

Falls et al., *Cell*, 72:801–815 (1993) describe another member of the neuregulin family which they call acetylcholine receptor inducing activity (ARIA) polypeptide. The chicken-derived ARIA polypeptide stimulates synthesis of muscle acetylcholine receptors. See also WO 94/08007. ARIA is a β-type neuregulin and lacks the entire "glyco" spacer (rich in glycosylation sites) present between the Ig-like domain and EGF-like domain of HRGα, and HRGβ1–β3.

Marchionni et al., *Nature*, 362:312–318 (1993) identified several bovine-derived proteins which they call glial growth factors (GGFs). These GGFs share the Ig-like domain and EGF-like domain with the other neuregulin proteins described above, but also have an amino-terminal kringle domain. GGFs generally do not have the complete "glyco" spacer between the Ig-like domain and EGF-like domain. Only one of the GGFs, GGFII, possessed a N-terminal signal peptide. See also WO 92/18627; WO 94/00140; and WO 94/04560 which refer to GGFs and uses thereof. Other polypeptides with mitogenic activity similar to GGFs have been described. For example, Beneniste et al., *PNAS, U.S.A.*, 82:3930–3934 (1985) describe isolation of a glial growth-promoting factor (GGPF) from human T-lymphocyte supernatant which has an apparent molecular weight of 30 kDa on non-reducing SDS-PAGE and 18 kDa on reducing SDS-PAGE. Furthermore, Davis and Stroobant, *J. Cell Biol.*, 110: 1353–1360 (1990) describe various growth factors which are mitogens for rat sciatic nerve Schwann cells in vitro, including GGF, TGF-β1 and TGF-β2.

(iii) Neuregulin Domains

The various neuregulin domains have been reviewed by Peles and Yarden in *Bioessays*, 15(12):815–824 (1993). These domains shall be briefly described below.

Inununoglobulin (Ig)-like domain—All of the identified neuregulins for which amino acid sequence data is available possess an Ig-like domain, suggesting this domain has an essential function. See Peles and Yarden, supra.

However, Kuo et al., by screening chick brain cDNA and human cerebellar cDNA libraries, recently identified a novel ARIA splice variant (called nARIA) which lacked the Ig-like domain of the other neuregulin polypeptides. Northern blot analysis localized expression of nARIA in the nervous system with particularly high levels detected in the cerebellum. Kuo et al., Abstract No. 452.18, *Soc. Neuroscience Abst.*, 20:1095 (1994). See also Yang et al., Abstract No. 452.17, *Soc. Neuroscience Abst.*, 20:1095 (1994).

Glycosylated spacer domain—This "glyco" domain, rich in N- and O-linked glycosylation sites, connects the Ig-like domain with the EGF-like domain. A single potential site for glycosaminoglycan attachment is present at the amino terminus of this spacer domain. ARIA and GGF lack 34-amino acid-residues of the glyco spacer, reducing the number of glycosylation sites in these molecules.

EGF-like domain—This region incorporates six cysteine residues and is predicted to fold into a structure having three disulfide-linked loops. As discussed above, neuregulins are classified as either α or β-type neuregulins based on the sequence of the C-terminal portion of the EGF-like domain. The EGF-like domain alone has been shown to bind with high affinity to the receptor. See Holmes et al., supra and Peles et al., *EMBO J.*, 12: 961–971 (1993). Sequence differences between the α and β forms apparently do not alter receptor specificity. However, the β form may bind with greater affinity to responsive cells than the α form.

The C-terminal portion of the EGF-like domain of some neuregulins is flanked by an eight-amino acid stretch. While this stretch of amino acid residues does not appear to affect receptor binding, it is thought to play a role in proteolytic processing of the precursor neuregulin to release the soluble polypeptide. See Peles and Yarden, supra.

Cytoplasmic tail—The transmembrane forms of neuregulins have four different hydrophilic cytoplasmic tails, the largest of which is 415 amino acid residues long. Some of the described neuregulins lack this cytoplasmic tail (e.g. HRG-β3 and GGFII).

(iv) Other Putative HER2 Activators

Other polypeptides which are considered to be HER2 activators have been described. Lupu et al., *Science*, 249:1552–1555 (1990) and Lupu et al., *Biochemistry*, 31:7330–7340 (1992) describe a 30 kDa glycoprotein (termed gp30) with TGF-α-like properties. Lupu et al. found that this factor stimulated phosphorylation of both the EGFR and p185$^{HER2}$. Lupu et al. isolated another growth factor from the conditioned medium of SK-BR-3 cells which they describe as binding to p185$^{HER2}$, but not EGFR. This factor, called p75, competed with the anti-HER2 receptor antibody 4D5 for p185$^{HER2}$ binding. Lupu et al., Abstract No. 297, *Proc. Am. Assoc. Cancer Res.*, 32 (1991). See also WO 91/18921; WO 92/12174; and WO 93/22339.

There has been another report of a glycoprotein which is able to activate both the EGFR and p185$^{HER2}$. This polypeptide had a molecular weight of 35 kDa and was heat stable but sensitive to reduction. See Yarden and Peles, *Biochemistry*, 30:3543–3550 (1991).

Tarakhovsky et al. describe a 25 kDa polypeptide secreted by activated mouse peritoneal macrophages, which is considered to be a ligand for p185$^{neu}$. Tarakhovsky et al., *Oncogene*, 6(12):2187–2196 (1991). Huang and Huang reported purification of a 25 kDa protein from bovine kidney which they call neu/erbB2 ligand growth factor (NEL-GF).

NEL-GFphosphorylated the neu receptor in intact NIH-3T3 cells expressing neu receptor.

Davis et al., *Biochem. Biophys. Res. Commun.*, 179(3):1536–1542 (1991) and Dobashi et al., *PNAS, U.S.A.*, 88:8582–8586 (1991) characterized a protein they call neu protein-specific activating factor (NAF) which had a molecular weight between about 8 to 24 kDa. NAF was said to activate p185$^{neu}$ but not the EGFR. See also WO 91/15230 to Greene et al. which mentions a 7–14 kDa polypeptide. In a later report, NAF is said to have a molecular weight of 15–17 kDa. Samanta et al., *PNAS, U.S.A.*, 91:1711–1715 (1994).

De Corte et al. recently reported the presence of a 50 kDa protein in conditioned medium of COLO-16 human cancer cells which appeared to activate the HER2 receptor in SK-BR-3 cells. Various biological activities including inducement of fast spreading, fast plasma membrane ruffling, cell shape change, net translocation, stimulation of chemotaxis and growth arrest in SK-BR-3 cells were attributed to this factor. De Corte et al., *J. Cell Science*, 107: 405–416 (1994).

(v) Biological Activities of Neuregulins

Diverse biological activities for the various neuregulin polypeptides have been described.

While the heregulin and NDF polypeptides were first identified based on their ability to activate p185$^{HER2/neu}$ (see Holmes et al., supra), it was discovered that certain ovarian cells expressing neu and neu-transfected fibroblasts did not bind or crosslink to NDF, nor did they respond to NDF to undergo tyrosine phosphorylation [Peles et al., *EMBO J.*, 12:961–971 (1993)]. This indicated another cellular component was necessary for conferring full neuregulin responsiveness. Carraway et al. subsequently demonstrated that $^{125}$I-rHRGβ1$_{177-244}$ bound to NIH-3T3 fibroblasts stably transfected with bovine erbB3 but not to non-transfected parental cells. Accordingly, they conclude that erbB3 is a receptor for HRG and mediates phosphorylation of intrinsic tyrosine residues as well as phosphorylation of p185$^{erbB2/neu}$ in cells which express both receptors. Caraway et al., *J. Biol. Chem.*, 269(19):14303–14306 (1994). Sliwkowski et al., *J. Biol. Chem.*, 269(20):14661–14665 (1994) found that cells transfected with HER3 alone show low affinities for heregulin, whereas cells transfected with both HER2 and HER3 show higher affinities.

This observation correlates with the "receptor cross-talking" described previously by Kokai et al., *Cell*, 58:287–292 (1989); Stern et al., *EMBO J.*, 7:995–1001 (1988); and King et al., 4:13–18 (1989). These researchers found that binding of EGF to the EGFR resulted in activation of the EGFR kinase domain and cross-phosphorylation of p185$^{neu}$. This is believed to be a result of ligand-induced receptor heterodimerization and the concomitant cross-phosphorylation of the receptors within the heterodimer [Wada et al., *Cell*, 61:1339–1347 (1990)].

Plowman and his colleagues have similarly studied p185$^{HER4}$/p185$^{HER2}$ activation. They expressed p185$^{HER2}$ alone, p185$^{HER4}$ alone, or the two receptors together in human T lymphocytes and demonstrated that neuregulin is capable of stimulating tyrosine phosphorylation of p185$^{HER4}$, but could only stimulate p185$^{HER2}$ phosphorylation in cells expressing both receptors. Plowman et al., *Nature*, 336:473–475 (1993). Thus, neuregulin is the only known example of a member of the EGF growth factor family that can interact with several receptors. Carraway and Cantley, *Cell*, 78:5–8 (1994).

The biological role of neuregulin has been investigated by several groups. For example, Falls et al., (discussed above) found that ARIA plays a role in myotube differentiation, namely affecting the synthesis and concentration of neurotransmitter receptors in the postsynaptic muscle cells of motor neurons. Corfas and Fischbach demonstrated that ARIA also increases the number of sodium channels in chick muscle. Corfas and Fischbach, *J. Neuroscience*, 13(5):2118–2125 (1993). It has also been shown that GGFII is mitogenic for subconfluent quiescent human myoblasts and that differentiation of clonal human myoblasts in the continuous presence of GGFII results in greater numbers of myotubes after six days of differentiation (Sklar et al., *J. Cell Biochem.*, Abst. W462, 18D, 540 [1994]).

Peles et al. (1992), supra, and Wen et al. (1992), supra, found that when certain mammary tumor cells (e.g. AU-565 and MDA-MB-453) were exposed to NDF, NDF induced phenotypic differentiation (including morphological changes and synthesis of milk components) and resulted in growth arrest. On the contrary, Holmes et al., supra, found that HRG exerted a mitogenic effect on mammary cell lines (such as SK-BR-3 and MCF-7).

The mitogenic activity of GGFs on Schwann cells has been reported. See, e.g., Brockes et al., *J. Biol. Chem.*, 255(18): 8374–8377 (1980); Lemke and Brockes, *J. Neurosci.*, 4:75–83 (1984); Brockes et al., *J. Neuroscience*, 4(1):75–83 (1984); Brockes et al., *Ann. Neurol.*, 20(3):317–322 (1986); Brockes, J., *Methods in Enzym.*, 147:217–225 (1987) and Marchionni et al., supra. Shah et al. report that GGF suppresses neuronal differentiation of rat neural crest stem cells but promotes or allows glial differentiation. Shah et al., *Cell*, 77:349–360 (1994).

Schwann cells constitute important glial cells which provide myelin sheathing around the axons of neurons, thereby forming individual nerve fibers. Thus, it is apparent that Schwann cells play an important role in the development, function and regeneration of peripheral nerves. The implications of this from a therapeutic standpoint have been addressed by Levi et al., *J. Neuroscience*, 14(3):1309–1319 (1994). Levi et al. discuss the potential for the construction of a cellular prosthesis comprising human Schwann cells which could be transplanted into areas of damaged spinal cord. Accordingly, these researchers outline the need for Schwann cell mitogens which can be used to allow full differentiation of these cells ex vivo. WO 94/00140 describes the use of various factors for stimulating mitogenesis of glial cells (e.g. Schwann cells). Others have demonstrated that heregulin is a potent mitogen for human Schwann cells in vitro. Levi et al., *J. Cell Biol.*, in press.

Pinkas-Kramarski et al. found that NDF seems to be expressed in neurons and glial cells in embryonic and adult rat brain and primary cultures of rat brain cells, and suggested that it may act as a survival and maturation factor for astrocytes (Pinkas-Kramarski et al., *PNAS, U.S.A.*, 91:9387–9391 [1994]). Meyer and Birchmeier, *PNAS, U.S.A.*, 91:1064–1068 (1994) analyzed expression of neuregulin during mouse embryogenesis and in the perinatal animal using in situ hybridization and RNase protection experiments. These authors conclude that, based on expression of this molecule, neuregulin plays a role in vivo as a mesenchymal and neuronal factor. Also, their findings imply that neuregulin functions in the development of epithelia. Similarly, Danilenko et al., Abstract 3101, *FASEB*, 8(4–5): A535 (1994), found that the interaction of NDF and the HER2 receptor is important in directing epidermal migration and differentiation during wound repair.

It is apparent from the above discussion that neuregulins, similar to other growth factors (e.g. interleukin-6 and amphiregulin), can act as differentiation factors or as mitogens depending on their concentration and on the cellular context.

Accordingly, it is an object of the present invention to identify a novel polypeptide activator of the HER2 receptor and/or a glial cell mitogen for diagnostic, ex vivo, and therapeutic uses.

It is yet another object to provide nucleic acid encoding such polypeptide and to use this nucleic acid to produce the polypeptide in recombinant cell culture.

It is a still further object to provide derivatives and modified forms of such polypeptide, including amino acid sequence variants and covalent derivatives thereof.

It is an additional object to prepare immunogens for raising antibodies against such polypeptides, as well as to obtain antibodies capable of binding them.

These and other objects of the invention will be apparent to the ordinarily skilled artisan upon consideration of the specification as a whole.

SUMMARY OF THE INVENTION

The invention provides isolated SMDF polypeptide. This SMDF polypeptide is preferably substantially homogeneous and may be selected from the group consisting of the native sequence polypeptide, a variant polypeptide, and a chimetic polypeptide. Additionally, the SMDF polypeptide may be selected from the group consisting of the polypeptide that is isolated from a mammal (e.g. a human), the polypeptide that is made by recombinant means, and the polypeptide that is made by synthetic means. Accordingly, the polypeptide may be unassociated with native glycosylation or may be completely unglycosylated. Further, this SMDF polypeptide may be selected from the group consisting of the polypeptide that is non-immunogenic in a human and SMDF having the translated amaino acid sequence of human SMDF shown in FIG. 1A (SEQ ID NO: 2).

In another aspect, the isolated SMDF polypeptide shares at least 75% amino acid sequence identity with the translated SMDF sequence shown in FIG. 1A (SEQ ID NO: 2).

In a still further aspect, the invention provides an isolated polypeptide encoded by a nucleic acid having a sequence that hybridizes under moderately stringent conditions to the nucleic acid sequence provided in FIG. 1A (SEQ ID NO: 1). Preferably, this polypeptide is biologically active.

In a still further aspect, the invention provides a composition comprising biologically active SMDF and a pharmaceutically acceptable carrier or comprising SMDF fused to an immunogenic polypeptide.

The invention also provides an assay for determining a prognosis in patients suffering from carcinoma (e.g. breast or ovarian carcinoma) which involves exposing a sample or cell from the patient to the SMDF mentioned above and determining the extent of SMDF binding to the sample or cell. Usually, the SMDF to be used in this assay will be labelled.

In another aspect, the invention involves activating HER2 receptor in vitro or in vivo, wherein a cell which expresses the HER2 receptor is exposed to SMDF polypeptide.

Also, it is possible to stimulate mitogenesis of a glial cell which is in cell culture or is present in a mammalian (especially human) patient by exposing it to SMDF.

In yet another aspect, the invention provides an isolated antibody that is capable of binding SMDF and a method for detecting SMDF in vitro or in vivo comprising contacting the antibody with a sample or cell suspected of Containing SMDF and detecting if binding has occurred, as with an ELISA.

In still another aspect, the invention provides a method for purifying SMDF comprising passing a mixture of SMDF over a column to which is bound the antibodies and recovering the fraction containing SMDF.

In other aspects, the invention comprises an isolated nucleic acid molecule encoding SMDF, a vector comprising the nucleic acid molecule, preferably an expression vector comprising the nucleic acid molecule operably linked to control sequences recognized by a host cell transformed with the vector, a host cell comprising the nucleic acid molecule, including mammalian and bacterial host cells, and a method of using a nucleic acid molecule encoding SMDF to effect the production of SMDF, comprising culturing a host cell comprising the nucleic acid molecule. Preferably the host cell is transfected to express SMDF nucleic acid and the SMDF is recovered from the host cell culture, and if secreted, recovered from the culture medium.

The isolated nucleic acid molecule may be selected from the group consisting of:

(a) a DNA comprising the nucleotide sequence of the coding region of the SMDF gene shown in FIG. 1A (SEQ ID NO: 1);

(b) a DNA corresponding to the sequence of (a) within the scope of degeneracy of the genetic code; and (c) a DNA which hybridizes to a sequence complementary to the DNA of (a) or (b) and which encodes a polypeptide possessing a biological property of a native sequence SMDF polypeptide.

In one embodiment, the invention provides a method for treating a mammal comprising administering a therapeutically effective amount of SMDF in a pharmaceutically acceptable carrier to the mammal. For example, the mammal may be suffering from a neurodegenerative disorder.

BRIEF DESCRIPTION OF THE DRAWINGS

FIG. 1A depicts the cDNA sequence [SEQ ID NO: 1] and amino acid sequence [SEQ ID NO: 2] of SMDF. In FIG. 1A, the EGF-like domain and the apolar and uncharged domains (i.e. "apolar I" consisting of residues from about 48–62 and "apolar II" consisting of residues from about 76–100) are underlined. Cysteines in the EGF-like domain and in the "cysteine knot" in the unique N-terminal domain ("NTD-cys knot") are boxed. The stop codon is denoted by the letter "O" (FIG. 1B depicts a hydropathy analysis of SMDF.

FIGS. 2A and 2B respectively show a diagramatic comparison of SMDF with GGFII, HRG-β1 and ARIA (FIG. 2A) and an amino acid sequence comparison of SMDF [SEQ ID NO: 2], GGFII [SEQ ID NO: 3], HRG-β1 [SEQ ID NO: 4] and ARIA [SEQ ID NO: 5] (FIG. 2B). In FIG. 2A, only major structural characteristics are shown. The EGF-like domain of SMDF is 100% identical to that of GGFII and HRG-βs, and 83% to ARIA at the nucleotide level. Like GGFII and HRG-β3, the SMDF sequence ends after the 8–10 amino acid stretch which connects the EGF-like domain with the transmembrane domain (TM), and is devoid of the latter and the cytoplasmic tail, which are present in HRG-β1 and ARIA. The sequence of SMDF N-terminal of the EGF-like domain (i.e. the unique "NTD") bears no identity to any known neuregulin. It lacks the Ig-like domain which is characteristic of all known neuregulins. It also lacks the N-terminal hydrophobic signal sequence of GGFII but possesses a stretch of apolar and uncharged amino acid residues (apolar II). In FIG. 2B, homologous Ig-like, EGF-like, and TM domains are boxed. The EGF-like domain of SMDF is identical to those of GGFII and HRG-β1, but differs from ARIA by 7 amino acids (denoted by *). GGFII and HRG-β1 have identical Ig-like domains and differ from ARIA by 30 and 35% at the nucleotide and amino acid (denoted by *) levels, respectively. SMDF has no Ig-like domain. The TM domains of HRG-β1 and ARIA are identical.

DETAILED DESCRIPTION OF THE PREFERRED EMBODIMENTS

I. Definitions

In general, the following words or phrases have the indicated definition when used in the description, examples, and claims:

"SMDF" (or "sensory and motor neuron derived factor") is defined herein to be any polypeptide sequence that possesses at least one biological property (as defined below) of native sequence SMDF comprising the polypeptide sequence of FIG. 1A (SEQ ID NO: 2). This definition encompasses not only the polypeptide isolated from a native SMDF source such as human brain described herein or from another source, such as another animal species, but also the polypeptide prepared by recombinant or synthetic methods. It also includes variant forms including functional derivatives, alleles, isoforms and analogues thereof. Preferably the SMDF is not chicken SMDF. Sometimes the SMDF is "native SMDF" which refers to endogenous SMDF polypeptide which has been isolated from a mammal. The SMDF can also be "native sequence SMDF" insofar as it has the same amino acid sequence as a native SMDF (e.g. human SMDF shown in FIG. 1A (SEQ ID NO: 2)). However, "native sequence SMDF" encompasses the polypeptide produced by recombinant or synthetic means.

Optionally, the SMDF is not associated with native glycosylation. "Native glycosylation" refers to the carbohydrate moieties which are covalently attached to native SMDF when it is produced in the mammalian cell from which the native SMDF is derived. Accordingly, human SMDF produced in a non-human cell could be described as not being associated with native glycosylation, for example. Sometimes, the SMDF is not associated with any glycosylation whatsoever (e.g. as a result of being produced recombinantly in a prokaryote).

SMDF shown in FIG. 1A (SEQ ID NO: 2) has a unique amino terminal domain which distinguishes this protein from previously described neuregulin proteins. This is designated the "N-terminal domain" or "NTD" herein (i.e. from about residue 1 to about residue 222 of FIG. 1A (SEQ ID NO: 2)). However, the expression "NTD" includes functional equivalents of the NTD depicted in FIG. 1A (SEQ ID NO: 2). This NTD has a "NTD-cysteine knot" or "NTD-cys knot" which is from about amino acid residue 58 to about residue 91 of FIG. 1A (SEQ ID NO: 2). Two domains which consist predominantly of apolar and uncharged amino acid residues are also present. These domains are designated "apolar I" (i.e. amino acid residues from about 48–62 of FIG. 1A (SEQ ID NO: 2)) and "apolar II" (i.e. amino acid residues from about 76–100 of FIG. 1A (SEQ ID NO: 2)) herein.

A "SMDF fragment" is a portion of a naturally occurring full-length SMDF sequence having one or more amino acid residues or carbohydrate units deleted. This term specifically excludes fragments consisting of the EGF-like domain only. The deleted amino acid residue(s) may occur anywhere in the polypeptide, including at either the N-terminal or C-terminal end or internally. Generally residues in the N-terminal domain will be deleted. The fragment will share at least one biological property in common with SMDF. SMDF fragments typically will have a consecutive sequence of at least 20, 30, or 40 amino acid residues of the NTD of SMDF. The preferred fragments have about 30–150 residues which are identical to the sequence of human SMDF. Other preferred SMDF fragments include those produced as a result of chemical or enzymatic hydrolysis or digestion of the purified SMDF. Exemplary fragments include SMDF with one of the apolar and uncharged domains (e.g. apolar I) deleted; and SMDF with the NTD-cys knot deleted.

"SMDF variants" or "SMDF sequence variants" as defined herein mean biologically active SMDFs as defined below having less than 100% sequence identity with the SMDF isolated from recombinant cell culture having the deduced amino acid sequence shown in FIG. 1A (SEQ ID NO: 2). Ordinarily, a biologically active SMDF variant will have an amino acid sequence having at least about 70% amino acid sequence identity with human SMDF shown in FIG. 1A (SEQ ID NO: 2), preferably at least about 75%, more preferably at least about 80%, still more preferably at least about 85%, even more preferably at least about 90%, and most preferably at least about 95%.

A "chimeric SMDF" is a polypeptide comprising full-length SMDF or one or more fragments thereof fused or bonded to a second protein or one or more fragments thereof. The chimera will share at least one biological property in common with SMDF. Examples of chimeric SMDFs include immunoadhesins and epitope tagged SMDF.

The term "immunoadhesin" is used interchangeably with the expression "SMDF-immunoglobulin chimera" and refers to a chimeric molecule that combines a biologically active portion of the SMDF with an immunoglobulin sequence. The immunoglobulin sequence preferably, but not necessarily, is an immunoglobulin constant domain. The immunoglobulin moiety in the chimeras of the present invention may be obtained from IgG-1, IgG-2, IgG-3 or IgG-4 subtypes, IgA, IgE, IgD or IgM, but preferably IgG-1 or IgG-3.

The term "epitope tagged" when used herein refers to a chimeric polypeptide comprising the entire SMDF, or a portion thereof, fused to a "tag polypeptide". The tag polypeptide has enough residues to provide an epitope against which an antibody thereagainst can be made, yet is short enough such that it does not interfere with activity of the SMDF. The tag polypeptide preferably is fairly unique so that the antibody thereagainst does not substantially cross-react with other epitopes. Suitable tag polypeptides generally have at least 6 amino acid residues and usually between about 8–50 amino acid residues (preferably between about 9–30 residues).

"Isolated SMDF", "highly purified SMDF" and "substantially homogeneous SMDF" are used interchangeably and mean SMDF that has been purified from a SMDF source or has been prepared by recombinant or synthetic methods and is sufficiently free of other peptides or proteins (1) to obtain at least 15 and preferably 20 amino acid residues of the N-terminal or of an internal amino acid sequence by using a spinning cup sequenator or the best commercially available amino acid sequenator marketed or as modified by published methods as of the filing date of this application, or (2) to homogeneity by SDS-PAGE under non-reducing or reducing conditions using Coomassie blue or, preferably, silver stain. Homogeneity here means less than about 5% contamination with other source proteins.

"Biological property" when used in conjunction with either "SMDF" or "isolated SMDF" means having an in vivo effector or antigenic function or activity that is directly or indirectly caused or performed by a SMDF (whether in its native or denatured conformation) or a fragment thereof. Effector functions include receptor activation (e.g. activation of the HER2, HER3 and/or HER4 receptor); enhancement of differentiation and/or proliferation of cells having one or more of these receptors (e.g. SK-BR-3 cells, Schwann cells, hepatocytes, glioblastoma cells, epithelial cells, muscle cells, astrocytes and/or oligodendrocytes); receptor binding (e.g. to the HER2, HER3 or HER4 receptor); mitogenic activity; inducing formation of ion channels (e.g. Na$^+$ channel) in a cell membrane; inducing acetylcholine receptor synthesis at the neuromuscular junction; enhancing formation of a synaptic junction between a neuron and a muscle, nerve or glandular cell; downregulation of estrogen receptor; and cell internalization (possibly associated with nuclear localization). However, effector functions do not include possession of an epitope or antigenic site that is capable of cross-reacting with antibodies raised against native sequence SMDF.

An "antigenic function" means possession of an epitope or antigenic site that is capable of cross-reacting with antibodies raised against native sequence SMDF. The principal antigenic function of a SMDF polypeptide is that it binds with an affinity of at least about $10^6$ L/mole to an antibody raised against native sequence SMDF. Ordinarily, the polypeptide binds with an affinity of at least about $10^7$ L/mole. The antibodies used to define "antigenic function" are rabbit polyclonal antibodies raised by formulating the native sequence SMDF in Freund's complete adjuvant, subcutaneously injecting the formulation, and boosting the immune response by intraperitoneal injection of the formulation until the titer of the anti-SMDF antibody plateaus.

"Biologically active" when used in conjunction with either "SMDF" or "isolated SMDF" means a SMDF polypeptide that exhibits or shares an effector function of SMDF isolated from a native source thereof or produced in recombinant cell culture described herein, and that may (but need not) in addition possess an antigenic function. Two principal effector functions of SMDF are its ability to activate the HER2 receptor and mitogenic activity on Schwann cells in culture.

"Antigenically active" SMDF is defined as a polypeptide that possesses an antigenic function of SMDF and that may (but need not) in addition possess an effector function.

"Percent amino acid sequence identity" with respect to the SMDF sequence is defined herein as the percentage of amino acid residues in the candidate sequence that are identical with the residues in the SMDF sequence having the deduced amino acid sequence described in FIG. 1A (SEQ ID NO: 2), after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the SMDF sequence shall be construed as affecting sequence identity or homology.

"Determining disease status" refers to the act of determining likelihood of patient survival and time to relapse for neoplastic diseases, particularly breast, ovarian, stomach, endometrial, salivary gland, lung, kidney, colon, and bladder carcinomas. In particular, SMDF can be used to quantify erbB receptor (e.g., erbB2, erbB3 or erbB4, but normally erbB2 receptor) overexpression in cancerous tissue taken from a patient suffering from carcinoma. This can also be referred to as "determining the proper course of treatment for patients suffering from cancer". For example, those patients characterized by erbB2 overexpression may require more aggressive treatment (e.g. chemo- or radiotherapy treatment) than might otherwise be indicated by other diagnostic factors. This phrase encompasses diagnosing patients suffering from high grade ductal carcinoma in situ. See, e.g., Disis et al., *Cancer Research*, 54:16–20 (1994).

The word "sample" refers to tissue, body fluid, or a cell from a patient. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues will be obtained and appropriately prepared. Other patient samples, including urine, serum, sputum, cell extracts etc will also be useful for particular tumors.

The expression "labelled" when used herein refers to a molecule (e.g. SMDF or anti-SMDF antibody) which has been conjugated, directly or indirectly, with a detectable compound or composition. The label may be detectable by itself (e.g. radioisotope labels or fluorescent labels) or, in the case of an enzymatic label, may catalyze a chemical alteration of a substrate compound or composition which is detectable. The preferred label is an enzymatic one which catalyzes a color change of a non-radioactive color reagent.

The phrase "activating HER2 receptor" refers to the act of causing the intracellular kinase domain of the HER2 receptor to phosphorylate tyrosine residues. Normally, the tyrosine residues will be present in the intracellular domain of the HER2 receptor which is activated (i.e. autophosphorylation), but it is possible that the receptor will phosphorylate residues in a substrate (such as an adjacent erbB receptor). erbB receptor autophosphorylation can be quantified using the KIRA-ELISA described herein.

By "stimulating mitogenesis of a glial cell" is meant enhancing proliferation of the glial cell in vitro or in vivo. The extent of cell proliferation can be measured using the glial cell proliferation assay herein described. A "glial cell" is derived from the central and peripheral nervous system and can be selected from oligodendroglial, astrocyte, ependymal, or microglial cells as well as satellite cells of ganglia and the neurolemmal or Schwann cells around peripheral nerve fibers.

"Isolated SMDF nucleic acid" is RNA or DNA containing greater than 16 and preferably 20 or more sequential nucleotide bases that encodes biologically active SMDF or a fragment thereof, is complementary to the RNA or DNA, or hybridizes to the RNA or DNA and remains stably bound under moderate to stringent conditions. This RNA or DNA is free from at least one contaminating source nucleic acid with which it is normally associated in the natural source and preferably substantially free of any other mammalian RNA or DNA. The phrase "free from at least one contaminating source nucleic acid with which it is normally associated" includes the case where the nucleic acid is present in the source or natural cell but is in a different chromosomal location or is otherwise flanked by nucleic acid sequences not normally found in the source cell. An example of isolated SMDF nucleic acid is RNA or DNA that encodes a biologically active SMDF sharing at least 75%, more preferably at least 80%, still more preferably at least 85%, even more preferably 90%, and most preferably 95% sequence identity with the human SMDF shown in FIG. 1A (SEQ ID NO: 2).

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

"Stringent conditions" are those that (1) employ low ionic strength and high temperature for washing, for example, 0.015M NaCl/0.0015M sodium citrate/0.1% NaDodSO$_4$ (SDS) at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC and 0.1% SDS.

"Moderately stringent conditions" are described in Sambrook et al., *Molecular Cloning: A Laboratory Manual* (New York: Cold Spring Harbor Laboratory Press, 1989), and include the use of a washing solution and hybridization conditions (e.g., temperature, ionic strength, and % SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37°–50° C. The skilled artisan will recognize how to adjust the temperature, ionic strength, etc., as necessary to accommodate factors such as probe length and the like.

The term "antibody" is used in the broadest sense and specifically covers single anti-SMDF monoclonal antibodies and anti-SMDF antibody compositions with polyepitopic specificity (including neutralizing and non-neutralizing antibodies).

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-SMDF antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments [e.g., Fab, F(ab)$_2$, and Fv], so long as they exhibit the desired biological activity. [See, e.g., U.S. Pat. No. 4,816,567 and Mage & Lamoyi, in *Monoclonal Antibody Production Techniques and Applications*, pp.79–97 (Marcel Dekker, Inc.), New York (1987)].

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods (U.S. Pat. No. 4,816,567). The "monoclonal antibodies" may also be isolated from phage libraries generated using the techniques described in McCafferty et al., *Nature* 348:552–554 (1990), for example.

"Humanized" forms of non-human (e.g. murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementary determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

By "neutralizing antibody" is meant an antibody molecule as herein defined which is able to block or significantly reduce an effector function of native sequence SMDF. For example, a neutralizing antibody may inhibit or reduce the ability of SMDF to activate the HER2 receptor in the KIRA-ELISA described herein. The neutralizing antibody may also block the mitogenic activity of SMDF in the glial cell proliferation assay detailed in this application.

"Non-immunogenic in a human" means that upon contacting the polypeptide in a pharmaceutically acceptable carrier and in a therapeutically effective amount with the appropriate tissue of a human, no state of sensitivity or resistance to the polypeptide is demonstrable upon the second administration of the polypeptide after an appropriate latent period (e.g., 8 to 14 days).

"Treatment" refers to both therapeutic treatment and prophylactic or preventative measures. Those in need of treatment include those already with the disorder as well as those prone to have the disorder or those in which the disorder is to be prevented.

"Manunal" for purposes of treatment refers to any animal classified as a mammal, including humans, domestic and farm animals, and zoo, sports, or pet animals, such as sheep, dogs, horses, cats, cows, etc. Preferably, the mammal herein is human.

II. Modes for Practicing the Invention

1. SMDF Polypeptides

The SMDF cloned from human brain has the following characteristics:

(a) it activates the HER2 receptor; and
(b) it displays mitogenic activity on rat Schwann cells in vitro.

The DNA (SEQ ID NO: 1) and amino acid (SEQ ID NO: 2) sequences of human SMDF are depicted in FIG. 1A. It is contemplated that the novel SMDF described herein may be a member of a family of growth factors having suitable sequence identity that their DNA may hybridize to the DNA in the unique N-terminal domain (NTD) of FIG. 1A (SEQ ID NO: 2) (or fragments thereof) under moderately stringent to stringent conditions. Thus, a further aspect of this invention includes DNA which hybridizes under moderately stringent to stringent conditions with the DNA encoding the NTD of SMDF. Techniques for isolating such native sequence SMDF molecules and making variant SMDF follow.

2. Preparation of Native Sequence SMDF and Variants

A. Isolation of DNA Encoding SMDF

The DNA encoding SMDF may be obtained from any cDNA library prepared from tissue believed to possess the SMDF mRNA and to express it at a detectable level. The mRNA is suitably prepared, for example, from a human brain stem cDNA library. The SMDF gene may also be obtained from a genomic library or by in vitro oligonucleotide synthesis assuming the complete nucleotide or amino acid sequence is known.

Libraries are screened with probes designed to identify the gene of interest or the protein encoded by it. For cDNA expression libraries, suitable probes include, e.g., monoclonal or polyclonal antibodies that recognize and specifically bind to the SMDF; oligonucleotides of about 20–80 bases in length that encode known or suspected portions of the SMDF cDNA from the same or different species; and/or complementary or homologous cDNAs or fragments thereof that encode the same or a similar gene. Appropriate probes for screening genomic DNA libraries include, but are not limited to, oligonucleotides, cDNAs, or fragments thereof that encode the same or a similar gene, and/or homologous genomic DNAs or fragments thereof. Screening the cDNA or genomic library with the selected probe may be conducted using standard procedures as described in chapters 10–12 of Sambrook et al., *Molecular Cloning: A Laboratory Manual* (New York: Cold Spring Harbor Laboratory Press, 1989).

An alternative means to isolate the gene encoding SMDF is to use PCR methodology as described in section 14 of Sambrook et al., supra. This method requires the use of oligonucleotide probes that will hybridize to the SMDF. Strategies for selection of oligonucleotides are described below.

A preferred method of practicing this invention is to use carefully selected oligonucleotide sequences to screen cDNA libraries from various tissues, preferably mammalian neural tissue. More preferably, human neural tissue cDNA libraries are screened with the oligonucleotide probes.

The oligonucleotide sequences selected as probes should be of sufficient length and sufficiently unambiguous that false positives are minimized. The actual nucleotide sequence(s) is usually based on conserved or highly homologous nucleotide sequences (e.g. encoding the NTD or a portion thereof). The oligonucleotides may be degenerate at one or more positions. The use of degenerate oligonucleotides may be of particular importance where a library is screened from a species in which preferential codon usage is not known.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Nucleic acid having all the native SMDF coding sequence is obtained by screening selected cDNA or genomic libraries using the deduced amino acid sequence disclosed herein for the first time, and, if necessary, using conventional primer extension procedures as described in section 7.79 of Sambrook et al., supra, to detect precursors and processing intermediates of mRNA that may not have been reverse-transcribed into cDNA.

B. Amino Acid Sequence Variants of Native Sequence SMDF

Amino acid sequence variants of native sequence SMDF are prepared by introducing appropriate nucleotide changes into the native sequence SMDF DNA, or by in vitro synthesis of the desired SMDF polypeptide. Such variants include, for example, deletions from, or insertions or substitutions of, residues within the amino acid sequence shown for human SMDF in FIG. 1A (SEQ ID NO: 2). Any combination of deletion, insertion, and substitution is made to arrive at the final construct, provided that the final construct possesses the desired characteristics. The amino acid changes also may alter post-translational processes of the native sequence SMDF, such as changing the number or position of O-linked glycosylation sites.

For the design of amino acid sequence variants of native sequence SMDF, the location of the mutation site and the nature of the mutation will depend on the SMDF characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the native SMDF polypeptide that are preferred locations for mutagenesis is called "alanine scanning mutagenesis," as described by Cunningham and Wells, *Science*, 244:1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis is conducted at the target codon or region and the SMDF variants produced are screened for the optimal combination of desired activity.

There are two principal variables in the construction of amino acid sequence variants: the location of the mutation site and the nature of the mutation. These are variants from the FIG. 1A sequence (SEQ ID NO: 2), and may represent naturally occurring alleles (which will not require manipulation of the native SMDF DNA) or predetermined mutant forms made by mutating the DNA, either to arrive at an allele or a variant not found in nature. In general, the location and nature of the mutation chosen will depend upon the SMDF characteristic to be modified.

Amino acid sequence deletions generally range from about 1 to 30 residues, more preferably about 1 to 10 residues, and typically are contiguous. Contiguous deletions ordinarily are made in even numbers of residues, but single or odd numbers of deletions are within the scope hereof. Deletions may be introduced into regions of low homology among various mammalian SMDFs to modify the activity of SMDF. Deletions from SMDF in the EGF-like domain will be more likely to modify the biological activity of SMDF more significantly. The number of consecutive deletions will be selected so as to preserve the tertiary structure of SMDF in the affected domain, e.g., beta-pleated sheet or alpha helix. An exemplary SMDF deletion mutant is SMDF with residues 286–296 terminal to the EGF-like domain deleted.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the mature SMDF sequence) may range generally from about 1 to 10 residues, more preferably 1 to 5, most preferably 1 to 3. Insertions are preferably made in even numbers of residues, but this is not required. Examples of terminal insertions include SMDF with an N-terminal methionyl residue, an artifact of the direct production of SMDF in recombinant cell culture. Other insertions are described below in Section J entitled "Chimeric SMDF".

A third group of variants are amino acid substitution variants. These variants have at least one amino acid residue in the native sequence SMDF molecule removed and a different residue inserted in its place. The sites of greatest interest for substitutional mutagenesis include sites identified as the active site(s) of native SMDF and sites where the amino acids found in the known analogues are substantially different in terms of side-chain bulk, charge, or hydrophobicity, but where there is also a high degree of sequence identity at the selected site within various animal SMDF species, or where the amino acids found in known neuregulins and SMDF are substantially different in terms of side-chain bulk, charge, or hydrophobicity, but where there also is a high degree of sequence identity at the selected site within various animal analogues of such neuregulins.

Other sites of interest are those in which particular residues of the SMDF obtained from various species are identical among all SMDFs, this degree of conformation suggesting importance in achieving biological activity common to these proteins. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitution |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the native sequence SMDF are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another. Such substituted residues also may be introduced into the conservative substitution sites or, more preferably, into the remaining (non-conserved) sites.

In one embodiment of the invention, it is desirable to inactivate one or more protease cleavage sites that are present in the molecule. These sites are identified by inspection of the encoded amino acid sequence, in the case of trypsin, e.g., for an arginyl or lysinyl residue. When protease cleavage sites are identified, they are rendered inactive to proteolytic cleavage by substituting the targeted residue with another residue, preferably a basic residue such as glutamine or a hydrophobic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

Any cysteine residues not involved in maintaining the proper conformation of native SMDF also may be substituted, generally with serine, to improve the oxidative stability of the molecule and prevent aberrant crosslinking.

Representative substitutions include human (i.e. hSMDF) SMDF [$A_{12} \rightarrow V$], hSMDF [$R_{47} \rightarrow K$], hSMDF [$D_{101} \rightarrow E$], hSMDF [$S_{149} \rightarrow Y$], hSMDF [$Y_{106} \rightarrow A$], hSMDF [$V_{163} \rightarrow L$], hSMDF [$N_{197} \rightarrow Q$], hSMDF [$V_{200} \rightarrow L$], hSMDF [$V_{235} \rightarrow T$], hSMDF [$E_{241} \rightarrow Q$], hSMDF [$F_{252} \rightarrow Y$], hSMDF [$K_{256} \rightarrow R$], hSMDF [$E_{199} \rightarrow D$], hSMDF [$Q_{158} \rightarrow N$], hSMDF [$T_{211} \rightarrow S$], hSMDF [$E_2 \rightarrow D$], hSMDF [$A_{171} \rightarrow V$], hSMDF [$A_{188} \rightarrow V$]. hSMDF with the β-type EGF-like domain substituted with an α-type EGF-like domain, and human SMDF with the β-type EGF-like domain replaced with the β-type EGF-like domain of rat NDF or ARIA.

Nucleic acid molecules encoding amino acid sequence variants of native sequence SMDF are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of native sequence SMDF.

Oligonucleotide-mediated mutagenesis is a preferred method for preparing substitution, deletion, and insertion variants of native SMDF DNA. This technique is well known in the art as described by Adelman et al., *DNA*, 2:183 (1983). Briefly, native SMDF DNA is altered by hybridizing an oligonucleotide encoding the desired mutation to a DNA template, where the template is the single-stranded form of a plasmid or bacteriophage containing the unaltered or native DNA sequence of SMDF. After hybridization, a DNA polymerase is used to synthesize an entire second complementary strand of the template that will thus incorporate the oligonucleotide primer, and will code for the selected alteration in the native SMDF DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75:5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al. *Meth. Enzymol.*, 153:3 (1987). Thus, the DNA that is to be mutated may be inserted into one of these vectors to generate single-stranded template. Production of the single-stranded template is described in Sections 4.21–4.41 of Sambrook et al., supra.

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of SMDF, and the other strand (the original template) encodes the native, unaltered sequence of SMDF. This heteroduplex molecule is then transformed into a suitable host cell, usually a prokaryote such as *E. coli* JM101. After the cells are grown, they are plated onto agarose plates and screened using the oligonucleotide primer radiolabeled with $^{32}P$ to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding mutants of native SMDF with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of native sequence SMDF. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 µg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 µL. The reaction mixture is overlayed with 35 µL mineral oil. The reaction mixture is denatured for five minutes at 100° C., placed briefly on ice, and then 1 µL *Thermus aquaticus* (Taq) DNA polymerase (5 units/µL, purchased from Perkin-Elmer Cetus) is added below the mineral oil layer. The reaction mixture is then inserted into a DNA Thermal Cycler (purchased from Perkin-Elmer Cetus) programmed as follows:

2 min. 55° C.

30 sec. 72° C., then 19 cycles of the following:

30 sec. 94° C.

30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., *Gene*, 34:315 (1985). The starting material is the plasmid (or other vector) comprising the native SMDF DNA to be mutated. The codon(s) in the native SMDF DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the native SMDF DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated SMDF DNA sequence.

C. Insertion of Nucleic Acid into Replicable Vector

The nucleic acid (e.g., cDNA or genomic DNA) encoding SMDF or SMDF variant is inserted into a replicable vector for further cloning (amplification of the DNA) or for expression. Many vectors are available, and selection of the appropriate vector will depend on 1) whether it is to be used for DNA amplification or for DNA expression, 2) the size of the nucleic acid to be inserted into the vector, and 3) the host cell to be transformed with the vector. Each vector contains various components depending on its function (amplification of DNA or expression of DNA) and the host cell with which it is compatible. The vector components generally include, but are not limited to, one or more of the following: an optional N-terminal signal sequence, an origin of replication, one or more marker genes, an enhancer element, a promoter, and a transcription termination sequence.

(i) Signal Sequence Component

The SMDFs of this invention may be produced not only directly, but also as a fusion with a heterologous polypeptide, preferably a signal sequence or other polypeptide having a specific cleavage site at the N-terminus of the mature protein or polypeptide. However, provision of a N-terminal signal sequence is optional since, without being limited to any one theory, SMDF appears to have an internal hydrophobic signal sequence.

In general, the signal sequence may be a component of the vector, or it may be a part of the SMDF DNA that is inserted into the vector. The heterologous signal sequence selected should be one that is recognized and processed (i.e., cleaved by a signal peptidase) by the host cell. For prokaryotic host cells, a prokaryotic signal sequence selected, for example, from the group consisting of the alkaline phosphatase, penicillinase, lpp, or heat-stable enterotoxin II leaders. For yeast secretion the yeast invertase leader, yeast alpha factor leader (including Saccharomyces and Kluyveromyces α-factor leaders, the latter described in U.S. Pat. No. 5,010, 182 issued 23 Apr. 1991), yeast acid phosphatase leader, mouse salivary amylase leader, carboxypeptidase leader, yeast BAR1 leader, Humicola lanuginosa lipase leader, the *C. albicans* glucoamylase leader (EP 362,179 published 4 Apr. 1990), or the signal described in WO 90/13646 published 15 Nov. 1990 are available. In mammalian cell expression, viral secretory leaders (for example, the herpes simplex gD signal) can be used, if desired.

The DNA for such precursor region is ligated in reading frame to DNA encoding SMDF.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 μ plasmid origin is suitable for yeast, and various viral origins (SV40, polyoma, adenovirus, VSV, or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of SMDF DNA. However, the recovery of genomic DNA encoding SMDF is more complex than that of an exogenously replicated vector because restriction enzyme digestion is required to excise the SMDF DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin (Southern et al., *J. Molec. Appl. Genet.*, 1:327 [1982]), mycophenolic acid (Mulligan et al., *Science*, 209:1422 [1980]), or hygromycin (Sugden et al., *Mol. Cell. Biol.*, 5:410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the SMDF nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes SMDF. Amplification is the process by which genes in greater demand for the production of a protein critical for growth are reiterated in tandem within the chromosomes of successive generations of recombinant cells. Increased quantities of SMDF are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci, U.S.A.*, 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding SMDF. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding SMDF, wild-type DHFR protein, and another selectable marker such as aminoglycoside 3-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282: 39 [1979]; Kingsman et al., *Gene*, 7:141 [1979]; or Tschemper et al., *Gene*, 10:157 [1980]). The trp1 gene provides a selection marker for a mutant strain of yeast lacking the ability to grow in tryptophan, for example, ATCC No. 44076 or PEP4-1 (Jones, *Genetics*, 85:12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Bianchi et al., *Curr. Genet.*, 12:185 (1987). More recently, an expression system for large-scale production of recombinant calf chymosin was reported for *K. lactis.*

Van den Berg, *Bio/Technology*, 8:135 (1990). Stable multicopy expression vectors for secretion of mature recombinant human serum albumin by industrial strains of Kluyveromyces have also been disclosed. Fleer et al., *Bio/Technology*, 9:968–975 (1991).

(iv) Promoter Component

Expression and cloning vectors usually contain a promoter that is recognized by the host organism and is operably linked to the SMDF nucleic acid. Promoters are untranslated sequences located upstream (5') to the start codon of a structural gene (generally within about 100 to 1000 bp) that control the transcription and translation of particular nucleic acid sequence, such as the SMDF nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to SMDF-encoding DNA by removing the promoter from the source DNA by restriction enzyme digestion and inserting the isolated promoter sequence into the vector. Both the native SMDF promoter sequence and many heterologous promoters may be used to direct amplification and/or expression of the SMDF DNA. However, heterologous promoters are preferred, as they generally permit greater transcription and higher yields of recombinantly produced SMDF as compared to the native SMDF promoter.

Promoters suitable for use with prokaryotic hosts include the β-lactamase and lactose promoter systems (Chang et al., *Nature*, 275:615 [1978]; and Goeddel et al., *Nature*, 281:544 [1979]), alkaline phosphatase, a tryptophan (trp) promoter system (Goeddel, *Nucleic Acids Res.*, 8:4057 [1980] and EP 36,776), and hybrid promoters such as the tac promoter (deBoer et al., *Proc. Natl. Acad. Sci. U.S.A.*, 80:21–25 [1983]). However, other known bacterial promoters are suitable. Their nucleotide sequences have been published, thereby enabling a skilled worker operably to ligate them to DNA encoding SMDF (Siebenlist et al., *Cell*, 20:269 [1980]) using linkers or adaptors to supply any required restriction sites. Promoters for use in bacterial systems also will contain a Shine-Dalgarno Dalgarno (S.D.) sequence operably linked to the DNA encoding SMDF.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255:2073 [1980]) or other glycolytic enzymes (Hess et al., *J. Adv. Enzyme Reg.*, 7:149 [1968]; and Holland, *Biochemistry*, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657. Yeast enhancers also are advantageously used with yeast promoters.

SMDF transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the SMDF sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209:1422–1427 (1980); Pavlakis et al., *Proc. Natl. Acad. Sci, U.S.A.*, 78:7398–7402 (1981). The immediate early promoter of the human cytomegalovirus is conveniently obtained as a HindIII E restriction fragment. Greenaway et al., *Gene*, 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295:503–508 (1982) on expressing cDNA encoding immune interferon in monkey cells; Reyes et al., *Nature*, 297:598–601 (1982) on expression of human β-interferon cDNA in mouse cells under the control of a thymidine kinase promoter from herpes simplex virus; Canaani and Berg, *Proc. Natl. Acad. Sci. U.S.A.*, 79:5166–5170 (1982) on expression of the human interferon β1 gene in cultured mouse and rabbit cells; and Gorman et al., *Proc. Natl. Acad, Sci. U.S.A.*, 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the SMDF of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. U.S.A.*, 78:993 [1981]) and 3' (Lusky et al., *Mol. Cell Bio.*, 3:1108 [1983]) to the transcription unit, within an intron (Banerji et al., *Cell*, 33:729 [1983]), as well as within the coding sequence itself (Osborne et al., *Mol. Cell Bio.*, 4:1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297:17-18 (1982) on enhancing elements for activation of eukaryotic promoters. The enhancer may be spliced into the vector at a position 5' or 3' to the SMDF-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding SMDF.

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9:309 (1981) or by the method of Maxam et al., *Methods in Enzymology*, 65:499 (1980).

(viii) Transient Expression Vectors

Particularly useful in the practice of this invention are expression vectors that provide for the transient expression in mammalian cells of DNA encoding SMDF. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of native sequence SMDF that are biologically active SMDF.

(ix) Suitable Exemplary Vertebrate Cell Vectors

Other methods, vectors, and host cells suitable for adaptation to the synthesis of SMDF in recombinant vertebrate cell culture are described in Gething et al., *Nature*, 293:620–625 (1981); Mantei et al., *Nature*, 281:40-46 (1979); EP 117,060; and EP 117,058. A particularly useful plasmid for mammalian cell culture production of SMDF is pRK5 (EP 307,247) or pSVI6B (WO 91/08291 published 13 Jun. 1991). The pRK5 derivative pRK5B (Holmes et al., *Science*, 253:1278–1280 [1991]) is particularly suitable herein for such expression.

D. Selection and Transformation of Host Cells

Suitable host cells for cloning or expressing the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published 12 Apr. 1989), Pseudomonas such as *P. aeruginosa*, and Streptomyces. One preferred *E. coli* cloning host is *E. coli* 294 (ATCC 31,446), although other strains such as *E. coli* B, *E. coli* X1776 (ATCC 31,537), *E. coli* DH5α, and *E. coli* W3110 (ATCC 27,325) are suitable. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonAα; *E. coli* W3110 strain 9E4, which has the complete genotype tonAα ptr3; *E. coli* W3110 strain 27C7 (ATCC 55,244), which has the complete genotype tonA ptr3 phoAΔE15 Δ(argF-lac)169 ΔdegP ΔompT kan$^r$; *E. coli* W3110 strain 37D6, which has the complete genotype tonA ptr3 phoAΔE15 Δ(argF-lac)169 ΔdegP ΔompT Δrbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for SMDF-encoding vectors. Saccharomyces cerevisiae, or common baker's yeast, is the most commonly used among lower eukaryotic host microorganisms. However, a number of other genera, species, and strains are commonly available and useful herein, such as *Schizosaccharomyces pombe* (Beach and Nurse, *Nature*, 290:140 [1981]; EP 139,383 published 2 May 1985); Kluyveromyces hosts (U.S. Pat. No. 4,943,529; Fleer et al., supra) such as, e.g., *K. lactis* (MW98-8C, CBS683, CBS4574; Louvencourt et al., *J. Bacteriol.*, 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*; yarrowia (EP 402,226); *Pichia pastoris* (EP 183,070; Sreekrishna et al., *J. Basic Microbiol.*, 28:265–278 [1988]); Candida; *Trichoderma reesia* (EP 244,234); *Neurospora crassa* (Case et al., *Proc. Natl. Acad. Sci. U.S.A.*, 76:5259–5263 [1979]); Schwanniomyces such as *Schwanniomyces occidentalis* (EP 394,538 published 31 Oct. 1990); and filamentous fungi such as, e.g., Neurospora, Penicillium, Tolypocladium (WO 91/00357 published 10 Jan. 1991), and Aspergillus hosts such as *A. nidulans* (Ballance et al., *Biochem. Biophys. Res. Commun.*, 112:284–289 [1983]; Tilburn et al., *Gene*, 26:205–221 [1983]; Yelton et al., *Proc. Natl. Acad. Sci. U.S.A.*, 81:1470–1474 [1984]) and *A. niger* (Kelly and Hynes, *EMBO J.*, 4:475–479 [1985]).

Suitable host cells for the production of SMDF are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes*

*albopictus* (mosquito), *Drosophila melanogaster* (fruitfly), and *Bombyx mori* have been identified. See, e.g., Luckow et al., *Bio/Technology,* 6:47–55 (1988); Miller et al., in *Genetic Engineering,* Setlow, J. K. et al., eds., Vol. 8 (Plenum Publishing, 1986), pp. 277–279; and Maeda et al., *Nature,* 315:592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the SMDF DNA. During incubation of the plant cell culture with *A. tumefaciens,* the DNA encoding the SMDF is transferred to the plant cell host such that it is transfected, and will, under appropriate conditions, express the SMDF DNA. In addition, regulatory and signal sequences compatible with plant cells are available, such as the nopaline synthase promoter and polyadenylation signal sequences. Depicker et al., *J. Mol. Appl. Gen.,* 1:561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure in recent years (*Tissue Culture,* Academic Press, Kruse and Patterson, editors [1973]). Examples of useful mammalian host cell lines are a monkey kidney CV1 cell line transformed by SV40 (COS-7, ATCC CRL 1651); a human embryonic kidney line (293 or 293 cells subcloned for growth in suspension culture, Graham et al., *J. Gen Virol.,* 36:59 [1977]); baby hamster kidney cells (BHK, ATCC CCL 10); Chinese hamster ovary cells/-DHFR (CHO, Urlaub and Chasin, *Proc. Natl. Acad. Sci. U.S.A.,* 77:4216 [1980]); mouse sertoli cells (TM4, Mather, *Biol. Reprod.,* 23:243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); TRI cells (Mather et al., *Annals N.Y. Acad. Sci.,* 383:44–68 [1982]); MRC 5 cells; FS4 cells; and a human hepatoma line (Hep G2).

Host cells are transfected with the above-described expression or cloning vectors of this invention and cultured in conventional nutrient media modified as appropriate for inducing promoters, selecting transformants, or amplifying the genes encoding the desired sequences.

Numerous methods of transfection are known to the ordinarily skilled artisan. For example, calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene,* 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Vilology,* 52:456–457 (1978) is preferred. General aspects of mammalian cell host system transformations have been described by Axel in U.S. Pat. No. 4,399,216 issued 16 August 1983. Transformations into yeast are typically carried out according to the method of Van Solingen et al., *J. Bact.,* 130:946 (1977) and Hsiao et al., *Proc. Natl. Acad. Sci. (U.S.A.),* 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology,* 185:527–537 (1990) and Mansour et al., *Nature,* 336:348–352 (1988).

E. Culturing the Host Cells

Prokaryotic cells used to produce the SMDF or SMDF variant are cultured in suitable media as described generally in Sambrook et al., supra.

The mammalian host cells used to produce the SMDF of this invention may be cultured in a variety of media. Commercially available media such as Ham's F-10 (Sigma), F-12 (Sigma), Minimal Essential Medium ([MEM], Sigma), RPMI-1640 (Sigma), Dulbecco's Modified Eagle's Medium ([D-MEM], Sigma), and D-MEM/F-12 (Gibco BRL) are suitable for culturing the host cells. In addition, any of the media described, for example, in Ham and Wallace, *Methods in Enzymology,* 58:44 (1979); Barnes and Sato, *Anal. Biochem.,* 102: 255 (1980); U.S. Pat. Nos. 4,767,704; 4,657,866; 4,927,762; 5,122,469; or 4,560,655; U.S. Pat. Re. No. 30,985; WO 90/03430; or WO 87/00195 may be used as culture media for the host cells. Any of these media may be supplemented as necessary with hormones and/or other growth factors (such as insulin, transferrin, aprotinin, and/or epidermal growth factor [EGF]), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of in vitro mammalian cell cultures can be found in *Mammalian Cell Biotechnology: a Practical Approach,* M. Butler, ed. (IRL Press, 1991).

The host cells referred to in this disclosure encompass cells in in vitro culture as well as cells that are within a host animal.

F. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. U.S.A.,* 77:5201–5205 [1980]), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75:734–738 (1980).

Antibodies useful for immunohistochemical staining and/ or assay of sample fluids may be either monoclonal or polyclonal, and may be prepared in any mammal. Conveniently, the antibodies may be prepared against a native sequence SMDF polypeptide or against a synthetic peptide based on the DNA sequences provided herein as described further in Section 7 below.

G. Purification of SMDF Polypeptide

SMDF preferably is recovered from the culture medium as a secreted polypeptide, although it also may be recovered from host cell lysates.

When SMDF is produced in a recombinant cell other than one of human origin, the SMDF is completely free of proteins or polypeptides of human origin. However, it is necessary to purify SMDF from cell proteins or polypeptides to obtain preparations that are substantially homogeneous as to SMDF. As a first step, the particulate debris, either host cells or lysed fragments, is removed, for example, by centrifugation or ultrafiltration; optionally, the protein may be concentrated with a commercially available protein concentration filter, followed by separating the SMDF from other impurities by one or more steps selected from heparin Sepharose chromatography, immunoaffinity chromatography, ion-exchange column fractionation (e.g., on DEAE or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the SMDF, and ethanol or ammonium sulfate precipitation. A protease inhibitor may be included in any of the foregoing steps to inhibit proteolysis and antibiotics may be included to prevent the growth of adventitious contaminants. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin, and benzamidine.

SMDF variants in which residues have been deleted, inserted, or substituted are recovered in the same fashion as native sequence SMDF, taking account of any substantial changes in properties occasioned by the variation. For example, preparation of a SMDF fusion with tag polypeptide, e.g., a bacterial or viral antigen, facilitates purification using an immunoaffinity column containing antibody to the antigen to adsorb the fusion polypeptide. Immunoaffinity columns such as a rabbit polyclonal anti-SMDF column can be employed to absorb the SMDF variant by binding it to at least one remaining immune epitope.

One skilled in the art will appreciate that purification methods suitable for native sequence SMDF may require modification to account for changes in the character of SMDF or its variants upon production in recombinant cell culture.

H. Covalent Modifications of SMDF Polypeptides

Covalent modifications of SMDF polypeptides are included within the scope of this invention. Both native sequence SMDF and amino acid sequence variants thereof may be covalently modified. One type of covalent modification included within the scope of this invention is the preparation of a SMDF fragment. SMDF fragments having up to about 40 amino acid residues may be conveniently prepared by chemical synthesis or by enzymatic or chemical cleavage of the full-length or variant SMDF polypeptide. Other types of covalent modifications of the SMDF or fragments thereof are introduced into the molecule by reacting targeted amino acid residues of the SMDF or fragments thereof with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl- 4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking SMDF to a water-insoluble support matrix or surface for use in the method for purifying anti-SMDF antibodies, and vice-versa. Commonly used crosslinking agents include, e.g., 1,1-bis(diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group.

Another type of covalent modification of the SMDF polypeptide included within the scope of this invention comprises altering the native glycosylation pattern of the polypeptide. By altering is meant deleting one or more carbohydrate moieties found in native sequence SMDF, and/or adding one or more glycosylation sites that are not present in the native sequence SMDF.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the SMDF polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native sequence SMDF sequence (for O-linked glycosylation sites). For ease, the native SMDF amino acid sequence is preferably altered through changes at the DNA level, particularly by mutating the DNA encoding the native sequence SMDF polypeptide at preselected bases such that codons are generated that will translate into the desired amino acids. The DNA mutation(s) may be made using methods described above under Section 2B.

Another means of increasing the number of carbohydrate moieties on the SMDF polypeptide is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.*, pp. 259–306 (1981).

Removal of any carbohydrate moieties present on the SMDF polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Glycosylation at potential glycosylation sites may be prevented by the use of the compound tunicamycin as described by Duskin et al., *J. Biol. Chem.*, 257:3105 (1982). Tunicamycin blocks the formation of protein-N-glycoside linkages.

Another type of covalent modification of SMDF comprises linking the SMDF polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

SMDF also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

I. Screening for Biologically Active SMDF Variants

Once amino acid sequence variants and covalent variants have been made, it is routine to screen for those molecules which are biologically and/or antigenically active. Competitive-type immunoassays as disclosed herein can be employed for determining whether the variant is able to cross-react with antibodies raised against native sequence SMDF (i.e. antigenically active SMDF). Two routine assays for screening for biologically active SMDF variants are described below. Other potential modifications of protein or polypeptide properties such as redox or thermal stability, hydrophobicity, susceptibility to proteolytic degradation, or the tendency to aggregate with carriers or into multimers are assayed by methods well known in the art.

(i) erbB Receptor KIRA-ELISA

This assay is useful for qualitatively and quantitatively measuring the ability of a SMDF variant to activate an erbB receptor. While the description that follows refers to the erbB2 receptor, the KIRA-ELISA can be readily modified to analyze activation of erbB3 or erbB4 receptors by the selected SMDF variants.

Polyclonal anti-HER2 antibody is isolated from pooled immune sera from New Zealand White rabbits immunized with the extracellular domain of the HER2 molecule (Fendly et al., *Journal of Biological Response Modifiers* 9:449–455 [1990]). The rHER2 ECD specific antibodies are affinity purified using an FPLC (Pharmacia Biotech, Inc, Piscataway, N.J.) with an affinity column generated from rHER2 ECD conjugated to Avidgel F (Bioprobe International, Inc, Tustin, Calif.). The resulting purified antibody stock in phosphate buffered saline (PBS), pH 7.4, is stored at −20° C. Monoclonal anti-phosphotyrosine, clone 4G10, can be purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio). SMDF is produced and purified to homogeneity as described above and is stored at 4° C. as a stock solution in Tris/HCl, pH 7.5, for example.

MCF-7 (ATCC-HTB 22), an adherent cell line isolated from a human breast adenocarcinoma, can be obtained from American Type Culture Collection (ATCC, Rockville, Md.). MCF-7 cells have been shown to produce measurable levels of $p185^{HER2}$ $p185^{HER3}$ and $p185^{HER4}$. The cells are maintained in tissue culture flasks (Corning Inc, Corning, N.Y.) and utilized when at cell densities of 60% to 75% confluency. Cells can be grown in F12/DMEM 50:50 (Gibco/BRL, Life Technologies, Grand Island, N.Y.). MCF-7 cells in media are added to each well in a flat-bottom-96 well culture plate and cultured overnight at 37° C. in 5% $CO_2$. The following morning the well supernatants are decanted, and the plates are lightly tamped on a paper towel. Media containing either culture medium (control), native sequence SMDF or variant SMDF is then added to each well. The cells are stimulated at 37° C. for about 30 min., the well supernatants are decanted, and the plates are once again lightly tamped on a paper towel. To lyse the cells and solubilize the receptors, 100 µl of lysis buffer is added to each well. Lysis buffer consists of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 µM leupeptin (ICN Biochemicals), and 2 mM sodium orthovanadate ($Na_3VO_4$, Sigma Chemical Co, St. Louis, Mo.), pH 7.5. The plate is then agitated gently on a plate shaker (Bellco Instruments, Vineland, N.J.) for 60 min. at room temperature.

While the cells are being solubilized, an ELISA microtiter plate (Nunc Maxisorp, Inter Med, Denmark) coated overnight at 4° C. with the affinity-purified polyclonal anti-HER2 ECD (in carbonate buffer, pH 9.6, 100 µl/well) is decanted, tamped on a paper towel and blocked with 150 µl/well of Block Buffer [PBS containing 0.5% BSA (Intergen Company, Purchase, N.Y.) and 0.01% thimerosal] for 60 min. at room temperature with gentle agitation. After 60 minutes, the anti-HER2 coated plate is washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized $p185^{HER2}$ from the cell-culture microtiter well is transferred (85 µl/well) to an anti-rHER2 coated and blocked ELISA well and is incubated for 2 h at room temperature with gentle agitation. The unbound receptor is removed by washing with wash buffer and 100 µl of biotinylated 4G10 (anti-phosphotyrosine antibody) in dilution buffer (PBS containing 0.5% BSA, 0.05% Tween-20, 5 mM EDTA, and 0.01% thimerosal), is added to each well. After incubation for 2 h at room temperature the plate is washed and 100 µl of HRPO-conjugated streptavidin (Zymed Laboratories, S. San Francisco, Calif.) in dilution buffer is added to each well. The plate is incubated for 30 minutes at room temperature with gentle agitation. The free avidin-conjugate is washed away and 100 µl freshly prepared substrate solution (tetramethyl benzidine [TMB]; 2-component substrate kit; Kirkegaard and Perry, Gaithersburg, Md.) is added to each well. The reaction is allowed to proceed for 10 minutes, after which the color development is stopped by the addition of 100 µl/well 1.0 M $H_3PO_4$. The absorbance at 450 nm is read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

Thus, the degree of erbB receptor autophosphorylation induced by the variant SMDF can be compared to that induced by native sequence SMDF, as well as the control (presumably no activation). Accordingly, variants which possess the biological property of activating an erbB receptor can be routinely identified.

(ii) Glial cell proliferation assay

In order to screen for biologically active variants, the following assay (optionally in combination with the KIRA-ELISA described above) is available.

Rat Schwann cells isolated from the sciatic nerves of two day old rats are purified free of contaminating fibroblasts and other cells [Brockes et al., *Brain Res.*, 165:105–118 (1979)], and grown in the presence of 3 nM rHRGβ1 (Holmes et al., supra). The cells are confirmed as Schwann cells by antibody staining of the Schwann cell surface marker $P75^{NGFR}$ [Brockes et al., *Nature*, 266: 364–366 (1977)]. Confluent cultures are washed twice with PBS, trypsinized and plated at $3.7 \times 10^4$ cells/well in a 24-well plate in serum-free transfection culture medium supplemented with insulin, transferrin, and trace elements. Duplicate wells are treated with SMDF variant, native sequence SMDF or control (e.g. serum-free medium only). Five days later, proliferation of the Schwann cells is quantified by microscopic examination of the degree of confluency.

Thus similarly to the above KIRA-ELISA assay, it is possible to identify those SMDF variants which share the biological activity of native sequence SMDF of stimulating mitogenesis of glial cells in cell culture.

J. Chimeric SMDF

This application encompasses chimeric polypeptides comprising SMDF fused to another polypeptide.

Chimeric SMDF polypeptides include fusions to the N- or C-terminus of native sequence SMDF of immunogenic polypeptides, e.g., bacterial polypeptides such as beta-lactamase or an enzyme encoded by the *E. coli* trp locus, or yeast protein, and C-terminal fusions with proteins such as albumin, or ferritin, as described in WO 89/02922 published 6 Apr. 1989.

In one preferred embodiment, the chimeric polypeptide comprises a fusion of the SMDF (or a fragment thereof) with a tag polypeptide which provides an epitope to which an anti-tag antibody can selectively bind. The epitope tag is generally proved at the amino- or carboxyl- terminus of the SMDF. Such epitope tagged forms of the SMDF are desirable, as the presence thereof can be detected using a labelled antibody against the tag polypeptide. Also, provision of the epitope tag enables the SMDF to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5, (Field et al., *Mol. Cell. Biol.* 8:2159–2165 [1988]); the c-myc tag and the 8F9, 3C7, 6E10, G4, B7 and 9E10 antibodies thereto (Evan et al., *Molecular and Cellular Biology* 5(12):3610–3616 [1985]); and the Herpes Simplex virus glycoprotein D (gD) tag and its antibody (Paborsky et al., *Protein Engineering* 3(6):547–553 [1990]). Other tag polypeptides have been disclosed. Examples include the Flag-peptide (Hopp et al., *BioTechnology* 6:1204–1210 [1988]); the KT3 epitope peptide (Martin et al., *Science* 255:192–194 [1992]); an α-tubulin epitope peptide (Skinner et al., *J. Biol. Chem* 266:15163–15166 [1991]); and the T7 gene 10 protein peptide tag (Lutz-Freyermuth et al., *Proc. Natl. Acad. Sci. USA* 87:6393–6397 [1990]). Once the tag polypeptide has been selected, an antibody thereto can be generated using the techniques disclosed herein.

The chimeric SMDF may also comprise an immunoadhesin having a longer half-life than native SMDF. Immunoadhesins constructed from a polypeptide linked to a heterologous immunoglobulin constant domain sequence are known in the art.

The simplest and most straightforward immunoadhesin design combines SMDF with the hinge and Fc regions of an immunoglobulin heavy chain. Ordinarily, when preparing the SMDF-immunoglobulin chimeras of the present invention, nucleic acid encoding the SMDF, or a fragment thereof, will be fused C-terminally to nucleic acid encoding the N-terminus of an immunoglobulin constant domain sequence. however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The general methods suitable for the construction and production of chimeric SMDF are the same as those disclosed hereinabove with regard to (native sequence or variant) SMDF. Chimeric SMDF is most conveniently constructed by fusing the cDNA sequence encoding the SMDF portion in-frame to the tag polypeptide or immunoglobulin DNA sequence, for example, and expressing the resultant DNA fusion construct in appropriate host cells.

Epitope tagged SMDF can be conveniently purified by affinity chromatography using the anti-tag antibody. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium.

Another type of chimeric SMDF which is encompassed by the present invention is SMDF conjugated with a toxic polypeptide such as those described below in the following section.

3. Therapeutic Compositions and Administration of SMDF

SMDF polypeptide is believed to find use as a drug for in vivo treatment of pathological diseases relating to the nervous system, usually neurodegenerative disorders (i.e. characterized by demyelination, damage and/or loss of neural tissue in the patient) and especially those diseases involving sensory and motor neurons. Accordingly, the SMDF polypeptide can be used for inducing neural regeneration and/or repair. Alternatively, the cDNA encoding SMDF can be used for gene therapy of such conditions.

Examples of diseases involving the sensory neurons which may be treated or ameliorated using SMDF include sensory neuropathy, e.g. diabetic neuropathy and drug-induced sensory neuropathy (e.g. resulting from chemotherapy).

SMDF may also be used for the treatment of disease states which involve motor neurons, i.e. characterized by degeneration of anterior horn cells of the spinal cord, the motor cranial nerve nuclei and the pyramidal tracts. Examples of such disease states include amyotrophic lateral sclerosis (ALS) or Lou Gehrig's disease, which is a syndrome involving muscular weakness and atrophy with spasticity and hyperreflexia. ALS is caused by degeneration of motor neurons of spinal cord, medulla, and cortex. If only cells of motor cranial nuclei in the medulla are involved, the condition is called progressive bulbar palsy. The SMDF may also be used to treat other diseases of the motor neurons including genetically-linked motor neuron diseases (e.g. Parkinson's disease), asymmetric motor neuropathy, progressive muscle atrophy, and conditions involving demyelination, damage or loss of glial cells (e.g. multiple sclerosis).

SMDF is also believed to find therapeutic use for treating peripheral nerve damage (e.g. giant axonal neuropathy, hereditary sensory hypertrophic neuropathy, and sensory neuropathy), leprous neuropathy, Landry-Guillain Barr syndrome, and neuropathy caused by carcinomas or toxic agents.

In some embodiments, it may be desirable to treat carcinomas characterized by erbB receptor overexpression using SMDF to direct a cytotoxic agent to the cancerous tissue. Examples of "cytotoxic agents" which can be conjugated with SMDF include cytotoxic drugs and radioactive molecules. For example the cytotoxic agent can be selected from an enzymatically active toxin of bacterial or plant origin or fragment thereof (e.g. diphtheria A chain, exotoxin A chain, ricin A chain, *Phytolacca americana* proteins, curcin, crotin, gelonin and abrin A chain). Alternatively, cytotoxic radiopharmaceuticals may be made by conjugating high linear energy transfer (LET) emitting isotopes (e.g. Y, Pr) to the SMDF.

Therapeutic formulations of SMDF are prepared for storage by mixing SMDF having the desired degree of purity with optional physiologically acceptable carriers, excipients, or stabilizers (*Remington's Pharmaceutical Sciences*, 16th Edition, Osol., A., Ed., [1980]), in the form of lyophilized cake or aqueous solutions. Pharmaceutically acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics, or polyethylene glycol (PEG).

SMDF to be used for in vivo administration must be sterile. This is readily accomplished by filtration through sterile filtration membranes, prior to or following lyophilization and reconstitution. SMDF ordinarily will be stored in lyophilized form or in solution.

Therapeutic SMDF compositions generally are placed into a container having a sterile access port, for example, an intravenous solution bag or vial having a stopper pierceable by a hypodermic injection needle.

The route of SMDF administration is in accord with known methods, e.g., injection or infusion by intravenous, intraperitoneal, intracerebral, intramuscular, intraocular, intraarterial, or intralesional routes, or by sustained-release systems as noted below. SMDF is administered continuously by infusion or by bolus injection.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15: 167–277 [1981] and Langer, *Chem. Tech.*, 12: 98–105 [1982] or poly (vinylalcohol)), polylactides (U.S. Pat. No. 3,773,919, EP 58,481), copolymers of L-glutamic acid and gamma ethyl-L-glutamate (Sidman et al., *Biopolymers*, 22:547–556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133, 988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release SMDF compositions also include liposomally entrapped SMDF. Liposomes containing SMDF are prepared by methods known per se: DE 3,218,121; Epstein et al., *Proc. Natl. Acad. Sci. USA*, 82: 3688–3692 (1985); Hwang et al., proc. *Natl. Acad. Sci. USA*, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal SMDF therapy.

An effective amount of SMDF to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg of patient body weight or more per day, preferably about 10 µg/kg/day to 10 mg/kg/day. Typically, the clinician will administer SMDF until a dosage is reached that achieves the desired effect for treatment of the above mentioned disorders.

4. Ex-Vivo Uses for SMDF

SMDF polypeptide can be used for growing glial cells ex vivo. It is desirable to have such populations of glial cells in cell culture for isolation of cell-specific factors e.g. $P75^{NGFR}$ which is a Schwann cell specific marker. Such factors are useful as diagnostic tools or, in the case of $P75^{NGFR}$, can be used an antigens to generate antibodies for diagnostic use. It is also desirable to have stable populations of glial cells in cell culture to facilitate characterization of other mitogens and growth inhibitory agents for these cells.

It is also beneficial to have populations of mammalian Schwann cells (preferably human Schwann cells) for use as cellular prostheses for transplantation into areas of damaged spinal cord in an effort to influence regeneration of interrupted central axons, for assisting in the repair of peripheral nerve injuries and as alternatives to multiple autografts. See Levi et al., (1994), supra. The use of cell culture techniques to obtain an abundant source of autologous graft material from a small biopsy has already met with clinical success in providing human epidermal cells to cover extensive burns (Gallico et al., *N. Eng J. Med.*, 311:338–451 [1984]). Furthermore, it has been shown that Schwann cells from human xenografts are capable of myelinating regenerating peripheral axons from mice which have been immunosuppressed (Aguayo et al., *Nature*, 268: 753–755 [1977], and Aguayo et al., *Soc. Neurosci. Symp.* 4:361–383 [1979]). Accordingly, it is expected that the above approach will meet with success in meals, including humans.

In order to generate such populations of glial cells, mammalian (e.g. human) peripheral nerves are obtained from donors. The nerves are harvested within 30 min of aortic clamping and stored in RPMI (GIBCO Laboratories, Grand Island, N.Y.) at 4° C. for not more than 24 hours. Each peripheral nerve is prepared for culture according to the protocol of Morrissey et al., *J. Neurosci*, 11:2433–2442 (1991). This includes washing the nerve three times in Lebovitz's L15 (GIBCO), stripping the epineurium of the nerve, and removing individual fascicles from the remaining interfascicular epineurium. The fascicles are cut into explants 2–4 mm long and placed in 35 mm culture dishes. The prepared nerves are kept in a humidified atmosphere with 5% $CO_2$ and the medium is replaced twice per week with Dulbecco's Modified Eagle's Medium (DMEM; GIBCO) with 10% fetal calf serum (FCS). The individual explants are transplanted to new dishes after a confluent nomolayer of predominantly fibroblasts (Fbs) has been generated as an outgrowth.

After one to three transplantations the nerve explants are dissociated according to the protocol of Pleasure et al., *Ann. NY Acad. Sci.*, 486:227–240 (1986). In brief, multiple explants are pooled and placed in 1–2 ml of an enzyme cocktail consisting of 1.25 U/ml dispase (Boehringer Mannheim Biochemicals, Germany), 0.05% collagenase (Worthington Biochemicals Corp., Freehold, N.J.) and 15.% FCS in DMEM. The explants are left in enzymes overnight and gently triturated the following morning with a straight glass borosilicate pipette, until individual explants can no longer be recognized. The cells are then washed in L15 and 10% FCS and plated on 100 mm culture dishes coated with 200 μm/ml poly-L-lysine (PLL; Sigma, St. Louis, Mo.).

The following day the cells are taken off the PLL-coated culture plates by rinsing twice with $Ca^{2+}$ and $Mg^{2+}$-free Hanks Balanced Salt Solution (HBSS; GIBCO) and exposing them to trypsin (0.05%) and EDTA (0.02%) (Sigma) in HBSS for 5–10 min at 37° C. The cells are collected and rinsed twice in L15 and 10% FCS, counted on a hemocytometer, and then diluted into a calculated volume of DMEM and 10% FCS (D10). The cells are then seeded on an Aclar (Allied Fiber and Plastics, Pottsville, Pa.) mini dishes coated with ammoniated collagen or PLL-coated culture dishes are then seeded on PLL-coated dishes and exposed to media containing D10 with SMDF (10 nM) cholera toxin (CT) Sigma, St. Louis, Mo. (100 ng/ml), and forskolin (1 μM) Sigma. The medium is changed three times per week and when the cells have reached confluency, they are taken up from the culture dishes with trypsin (0.05%)/EDTA(0.02%) solution.

The cells which are thus generated in cell culture are then surgically placed in patients.

In another embodiment of the invention, growth of breast cancer cell lines (e.g. SK-BR-3 cells) which overexpress the HER2 receptor can be stimulated in vitro using SMDF. This is useful insofar as this cell line is a source of the HER2 receptor and this receptor can be isolated, antibodies can be generated thereagainst (using the techniques for generating antibodies described herein), and these antibodies can be used as diagnostic tools for diagnosing HER2 overexpression as disclosed in U.S. Pat. No. 4,968,603.

5. Diagnostic Uses for SMDF

SMDF can be used in the diagnosis of cancers characterized by erbB receptor (e.g. erbB2 receptor) overexpression and/or amplification. This diagnostic assay can be used in combination with other diagnostic/prognostic evaluations such as determining lymph node status, primary tumor size, histologic grade, estrogen or progesterone status, tumor DNA content (ploidy), or cell proliferation (S-phrase fraction). See Muss et al., *New Eng, J, Med.*, 330(18): 1260–1266 (1994). HER2 overexpression suggests that the disease is more likely to spread beyond the primary tumor site and patients who test positively for HER2 receptor overexpression will usually relapse more quickly after surgical removal of the tumor. See U.S. Pat. No. 4,968,603. Therefore, more aggressive treatment (e.g. chemo- or radiation therapy) may be chosen if HER2 overexpression is identified. Also, cancers characterized by HER2 overexpression may constitute candidates for treatment with the anti-HER2 antibody, 4D5, disclosed in Shepherd et al., *J. Clin. Immunol.*, 11(3): 117–127 (1991).

The sample as herein defined is obtained, e.g. tissue sample from the primary lesion of a patient. Formalin-fixed, paraffin-embedded blocks are prepared. See Muss et al., supra and Press et al., *Cancer Research*, 54:2771–2777 (1994). Tissue sections (e.g. 4 μM) are prepared according to known techniques. The extent of SMDF binding to the tissue sections is then quantified.

Generally, the SMDF will be labelled either directly or indirectly with a detectable label. Numerous labels are available which can be generally grouped into the following categories (these labels are also useful for labelling SMDF antibodies which will be described below):

(a) Radioisotopes, such as $^{35}S$, $^{14}C$, $^{125}I$, $^{3}H$, and $^{131}I$. The SMDF or antibody can be labeled with the radioisotope using the techniques described in *Current Protocols in Immunology*, Ed. Coligen et al., Wiley Publishers, Vols 1 & 2, for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the SMDF or antibody using the techniques disclosed in *Current Protocols in Immunology*, supra, for example. Fluorescence can be quantified using a fluorimeter (Dynatech).

(c) Various enzyme-substrate labels are available and U.S. Pat. No. 4,275,149 provides a review of some of these. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a Dynatech ML3000 chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to proteins are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147–166 (1981) and *Current Protocols in Immunology*, supra.

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine [OPD] or 3,3',5,5'-tetramethyl benzidine hydrochloride [TMB]).

(ii) alkaline phosphatase (AP) with para-Nitrophenyl phosphate as chromogenic substrate.

(iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the SMDF or antibody. The skilled artisan will be aware of various techniques for achieving this. For example, the SMDF or antibody can be conjugated with biotin and any of the three broad categories of labels mentioned above can be conjugated with avidin, or vice versa. Biotin binds selectively to avidin and thus, the label can be conjugated with the SMDF or antibody in this indirect manner. See, *Current Protocols in Immunology*, supra, for a review of techniques involving biotin-avidin conjugation. Alternatively, to achieve indirect conjugation of the label with the SMDF or antibody, the SMDF or antibody is conjugated with a small hapten (e.g. digoxin) and one of the different types of labels mentioned above is conjugated with an anti-hapten antibody (e.g. anti-digoxin antibody). Thus, indirect conjugation of the label with the SMDF or antibody can be achieved.

In another embodiment of the invention, the SMDF need not be labeled, and the presence thereof can be detected using a labeled anti-SMDF antibody (e.g. conjugated with HRPO).

In the preferred embodiment, the SMDF or antibody is labeled with an enzymatic label which catalyzes a color change of a substrate (such as tetramethyl benzimidine [TMB], or orthaphenylene diamine [OPD]). Thus, the use of radioactive materials is avoided. A color change of the reagent can be determined spectrophotometrically at a suitable wavelength (e.g. 450 nm for TMB and 490 nm for OPD, with a reference wavelength of 650 nm).

Thus, the tissue sections on slides are exposed to the labelled SMDF and the intensity of staining of the tissue sections is determined. While in vitro analysis is normally contemplated, in vivo diagnosis using SMDF conjugated to a detectable moiety (e.g. In for imaging) can also be performed. See, e.g., U.S. Pat. No. 4,938,948.

6. Other Non-therapeutic Uses for SMDF

SMDF preparations are useful as standards in assays for SMDF (e.g., by labeling SMDF for use as a standard in a radioimmunoassay, enzyme-linked immunoassay, or radioreceptor assay), in affinity purification techniques (e.g. for an erbB receptor such as erbB3 or erbB4 receptor), and in competitive-type receptor binding assays when labeled with radioiodine, enzymes, fluorophores, spin labels, and the like. SMDF polypeptides are also useful as immunogens for generating anti-SMDF antibodies for diagnostic use.

Similarly, the nucleic acid encoding SMDF is useful as a probe for detecting SMDF expression in various tissues. Thus, SMDF-specific probes are useful for tissue typing (e.g. for identifying sensory and motor neuron tissue) either in vitro or in vivo. In this respect, nucleic acid encoding the unique NTD of SMDF or fragments thereof (e.g. the NTD-cys knot, apolar I or apolar II domains) are particularly useful tissue-specific markers. Techniques for DNA analysis are well known. See, e.g. U.S. Pat. No. 4,968,603. Normally, the DNA analysis will involve Southern blotting a sample derived from a mammal. Alternatively, SMDF-specific antibodies can be used for tissue-specific typing.

7. SMDF Antibody Preparation

A. Polyclonal antibodies

Polyclonal antibodies to SMDF polypeptides or SMDF fragments are generally raised in animals by multiple subcutaneous (sc) or intraperitoneal (ip) injections of SMDF or SMDF fragment and an adjuvant. It may be useful to conjugate SMDF or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the SMDF polypeptide or SMDF fragment, immunogenic conjugates, or derivatives by combining 1 mg or 1 µg of the peptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for SMDF or SMDF fragment antibody titer. Animals are boosted until the titer plateaus. Preferably, the animal is boosted with the conjugate of the same SMDF or SMDF fragment, but conjugated to a different protein and/or through a different cross-linking reagent. Conjugates also can be made in recombinant cell culture as protein fusions. Also, aggregating agents such as alum are suitably used to enhance the immune response.

B. Monoclonal antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the SMDF monoclonal antibodies of the invention may be made using the hybridoma method first described by Kohler and Milstein, *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the SMDF or SMDF fragment used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Culture medium in which hybridoma cells are growing is assayed for production of monoclonal antibodies directed against SMDF. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard, *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256–262 (1993) and Plückthun, *Immunol. Revs.*, 130:151–188 (1992).

The DNA also may be modified, for example, by substituting the coding sequence for human heavy- and light-chain constant domains in place of the homologous murine sequences (Morrison, et al., *Proc. Nat. Acad. Sci.*, 81:6851 [1984]), or by covalently joining to the immunoglobulin coding sequence all or part of the coding sequence for a non-immunoglobulin polypeptide. In that manner, "chimeric" or "hybrid" antibodies are prepared that have the binding specificity of an anti-SMDF monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a SMDF and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include imunothiolate and methyl-4-mercaptobutyrimidate.

C. Humanized antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321, 522–525 [1986]; Riechmann et al., *Nature*, 332, 323–327 [1988]; and Verhoeyen et al., *Science*, 239, 1534–1536 [1988]), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 [1993]; and Chothia and Lesk, *J. Mol. Biol.*, 196:901 [1987]). Another method uses a particular framework derived from the consensus sequence of all human antibodies of a particular subgroup of light or heavy chains. The same framework may be used for several different humanized antibodies (Carter et al., *Proc. Natl. Acad. Sci, USA*, 89:4285 [1992]; and Presta et al., *J. Immnol.*, 151:2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

D. Human antibodies

Human monoclonal antibodies can be made by the hybridoma method. Human myeloma and mouse-human heteromyeloma cell lines for the production of human monoclonal antibodies have been described, for example, by Kozbor, *J. Immunol.*, 133, 3001 (1984); Brodeur, et al., *Monoclonal Antibody Production Techniques and Applications*, pp.51–63 (Marcel Dekker, Inc., New York, 1987); and Boerner et al., *J. Immunol.*, 147:86–95 (1991).

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such gem-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255–258 (1993); and Bruggermann et al., *Year in Immuno.*, 7:33 (1993).

Alternatively, phage display technology (McCafferty et al., *Nature*, 348: 552–553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimicks some of the properties of the B-cell. Phage display can be performed in a variety of formats; for their review see, e.g., Johnson, Kevin S. and Chiswell, David J., *Current Opinion in Structural Biology*, 3:564–571 (1993). Several sources of V-gene segments can be used for phage display. Clackson et al., *Nature*, 352: 624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.*, 222:581–597 (1991), or Griffith et al., *EMBO J.*, 12:725–734 (1993).

In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.*, 10:779–783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires has been described by Waterhouse et al., *Nucl. Acids Res.*, 21:2265–2266 (1993).

Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT WO 93/06213, published 1 Apr. 1993). Unlike traditional humanization of rodent antibodies by CDR grafting, this technique provides completely human antibodies, which have no framework or CDR residues of rodent origin.

E. Bispecific antibodies

Bispecific antibodies are monoclonal, preferably human or humanized, antibodies that have binding specificities for at least two different antigens. In the present case, one of the binding specificities is for a SMDF, the other one is for any other antigen, and preferably for another polypeptide that activates an erbB receptor. For example, bispecific antibodies specifically binding SMDF and a neuregulin are within the scope of the present invention.

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature*, 305:537–539 [1983]). Because of the random assortment of immunoglobulin heavy and light chains, these hybridomas (quadromas) produce a potential mixture of 10 different antibody molecules, of which only one has the correct bispecific structure. The purification of the correct molecule which is usually done by affinity chromatography steps, is rather cumbersome, and the product yields are low. Similar procedures are disclosed in WO 93/08829 and in Traunecker et al., *EMBO J.*, 10: 3655–3659 (1991).

According to a different and more preferred approach, antibody-variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1), containing the site necessary for light-chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the production of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation.

For further details of generating bispecific antibodies, see, for example, Suresh et al., *Methods in Enzymology*, 121:210 (1986).

F. Heteroconjugate antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/00373; and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

G. Neutralizing Antibodies

To manufacture a neutralizing antibody, antibodies are made using the techniques for generating these molecules elaborated above. The preferred neutralizing antibody is non-immunogenic in a human and directed against a single determinant. Following production of a panel of antibodies, the molecules are subjected to a screening process in order to identify those molecules which meet the desired criteria (i.e. which are able to neutralize a biological activity of SMDF either in vitro or in vivo). Normally, samples of SMDF will be exposed to the panel of anti-SMDF antibodies and will then be subjected to either or both of the erbB receptor KIRA-ELISA and glial cell proliferation assay described herein. Those antibodies which block the ability of SMDF to activate the HER2 receptor and/or mitogenic activity of SMDF on glial cells can be selected as neutralizing antibodies.

8. Uses for SMDF Antibodies

SMDF antibodies are useful in diagnostic assays for SMDF, e.g., its production in specific cells, tissues, or serum. For example, SMDF antibodies can be used for tissue typing (e.g. for identifying sensory and motor neurons). The antibodies are labeled in the same fashion as SMDF described above and/or are immobilized on an insoluble matrix.

Suitable diagnostic assays for SMDF and its antibodies are well known per se. Analytical methods for SMDF or its antibodies all use one or more of the following reagents: labeled analyte analogue, immobilized analyte analogue, labeled binding partner, immobilized binding partner, and steric conjugates. The labeled reagents also are known as "tracers."

The label used is any detectable functionality that does not interfere with the binding of analyte and its binding partner. Numerous labels are known for use in immunoassays and have been described in Section 5 above. Those of ordinary skill in the art will know of other suitable labels that may be employed in accordance with the present invention. These labels can be conjugated to SMDF antibodies using standard techniques commonly known to those of ordinary skill in the art.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte, the presence of the anti-analyte modifies the enzyme activity. In this case, SMDF or its immunologically active fragments are conjugated with a bifunctional organic bridge to an enzyme such as peroxidase. Conjugates are selected for use with anti-SMDF so that binding of the anti-SMDF inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of SMDF or SMDF antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-SMDF monoclonal antibody as one antibody and a polyclonal anti-SMDF antibody as the other is useful in testing samples for SMDF activity.

SMDF antibodies also are useful for the affinity purification of SMDF from recombinant cell culture or natural sources.

Neutralizing anti-SMDF antibodies may also be used to block SMDF biological activity in vivo. For example, the antibodies can be used to block SMDF activation of erbB receptor (e.g. erbB2 receptor) in certain cancers involving SMDF activation of the receptor(s). Thus, the neutralizing antibodies may be used in the treatment or amelioration of certain glial cell tumors.

9. Kits

Since the invention provides at least two types of diagnostic assay (i.e. for determining disease status using SMDF or determining SMDF using antibodies or DNA markers) as a matter of convenience, the reagents for these assays can be provided in a kit, i.e., a packaged combination of reagents, for combination with the sample to be tested. The components of the kit will normally be provided in predetermined ratios. Thus, a kit may comprise the antibody or SMDF (DNA or polypeptide) labelled directly or indirectly with a suitable label. Where the detectable label is an enzyme, the kit will include substrates and cofactors required by the enzyme (e.g. a substrate precursor which provides the detectable chromophore or fluorophore). In addition, other additives may be included such as stabilizers, buffers and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. The kit also suitably includes instructions for carrying out the bioassay.

The following examples are offered by way of illustration and not by way of limitation. The disclosures of all citations in the specification are expressly incorporated herein by reference.

EXAMPLE 1

Isolation of SMDF cDNA Clones

Two degenerate oligonucleotides corresponding to A) a portion of coding segment 1 (nt 739–825) and B) a portion of coding segments 8 and 9 (nt 1452–1507) of the neuregulin gene (Marchionni et al., supra) were labeled by random oligonucleotide priming and used simultaneously to screen $5.5 \times 10^6$ plaques from two human brain stem cDNA libraries (LMG2, ATCC 37432, in λgt11; and Strategene, in λZAP) and a human cerebellum (Clontech, 5'-stretch, in λgt11) cDNA library. Positive clones were isolated by repetitive screening. Initially 13 clones were isolated: 3 hybridized to both probes, 4 hybridized to probe A only, and 6 hybridized to probe B only. The insert size was estimated after EcoR I digestion of purified phage DNA. The insert of each clone was subcloned into the plasmid pBluescript SK(−) (Stratagene) at the EcoR I site and subjected to DNA sequence analysis. After initial analysis, 7 clones were selected for full sequence analysis.

Nucleotide sequences were determined by the dideoxy chain termination method (Sanger et al., PNAS, USA, 74:5463–5467 [1977]) using a 70770 Sequenase version 2.0 DNA sequencing kit (US Biochemicals). Both strands of the inserts were sequenced. Nucleotide sequences were analyzed using the Sequence Analysis Program (Genentech Scientific Computing Group).

One of the resulting clones which hybridized strongly to both probes was a full length clone (clone BS4). Three of the clones which hybridized to probe B only were full length clones (clones BS1, BS2, BS3). Two of the clones (BS5, BS6) which hybridized to probe B only and one clone (CB2) which hybridized to both probes were incomplete clones.

Among the complete clones, BS4 had an identical sequence to human GGF (GGFHBS5) of Marchionni et al., supra. BS1, BS2, and BS3 are three independent clones, two of which (BS1, 2) show identical coding sequences. The coding sequence of BS3 differs from BS1 and BS2 at amino acid residues 171 and 188 both of which are Ala to Val substitutions. Except for 18 nt adjacent to the 5' polycloning site, BS1 and BS2 have nearly homologous 5' untranslated sequences. The 5' untranslated sequence of BS3 is 109 nt shorter but otherwise differs from those of BS1 and BS2 by 12 nt only.

FIG. 1A shows the nucleotide sequence (SEQ ID No. 2) of the BS1 cDNA and its predicted amino acid sequence (SEQ ID No. 2). Beginning with the ATG at nt 507 (BS1), 264 (BS2), and 522 (BS3), each of which starts the only extensive open reading frame, the BS1, BS2, and BS3 cDNAs each encode a polypeptide of 296 amino acids, with a predicted Mr of 31,686Da. The stop codon is followed by a 478 (BS1), 382 (BS2), and 120 nt (BS3) 3' untranslated sequence ending with an A-rich region in BS1 (short stretch) and BS2 (long stretch) preceded by 2–3 consensus polyadenylation signal AATAAA. BS3 has no polyadenylation signal or A-rich region.

A diagramatic comparison of SMDF, GGFII, HRGβ1, and ARIA is shown in FIG. 2A (only major structural characteristics are shown); and a comparison of the amino acid sequences of the above four proteins is shown in FIG. 2B. The SMDF protein (SEQ ID Nos. 2, 3, 4 and 5) has an EGF-like domain that shares 100% sequence identity with those of GGFII (Marchionni et al., supra), HRG-β1, β2, β3 (Holmes et al., supra), and human NDF-β1a, -β2, -β3 (Wen et al. [1994] supra); 92% with some rat NDFs (clones 22, 40, 41, 42a); and 83% with ARIA. However, a comparison with the GenBank nucleotide database and protein database using the BLAST program shows that the SMDF sequence N-terminal to the EGF-like domain is novel, and distinct from all other reported neuregulin sequences. Like HRG, NDF, and ARIA, SMDF is also devoid of a N-terminal signal peptide typical of membrane and secreted proteins. Like some variants (among which include HRG-β3 and GGFII), the SMDF sequence ends after the 8–10 variable amino acid stretch which connects the EGF-like domain with the transmembrane domain, and is therefore devoid of the latter and the cytoplasmic tail. The major structural difference between SMDF and the neuregulins is the lack in SMDF of an Ig-like domain characteristic of all the other neuregulins. Another feature of SMDF distinct from the neuregulins is the apparent lack of a region rich in N-linked glycosylation sites (although there appear to be abundant O-linked sites). A third notable feature of SMDF is the presence of two stretches of amino acids near the N-terminus, residues T48-L62 (i.e., apolar I) and I76-V100 (i.e., apolar II), that are predominantly hydrophobic in nature (see hydropathy analysis, FIG. 1B). Without being limited to any particular theory, it is possible that these sequences, in particular I76-V100, may act like internal, uncleaved signal sequences that may mediate the translocation across the endoplasmic reticulum membrane (Blobel, PNAS, USA, 77:1496–1500 [1980]; Sabatini et al., J. Cell Biol., 92:1–22 [1982]; Wickner and Lodish, Science, 230:400–407 [1985]; and von Heijne, Biochim. Biophys. Acta, 947:307–333 [1988]). The presence of positively and negatively charged residues upstream of this hydrophobic stretch in SMDF befits the typical features of internal uncleaved signal peptides (von Heijne, supra). Examples of such uncleaved, internal signal peptides are the hydrophobic signal element near the N-terminus of ovalbumin (Meek et al., J. Biol. Chem., 257: 12245–12251 [1982]) and synaptotagmin (Perin et al., J. Biol. Chem., 266:623–629 [1991]). A fourth notable feature is the presence of eight cysteine residues scattered along the hydrophobic stretch (i.e. the "NTD-cys knot").

EXAMPLE 2

Expression of SMDF in Mammalian Cells

A fragment of cDNA corresponding to the entire coding sequence of the human SMDF clone BS1 with added 5'-Sal I and 3'- Hind III restriction sites for ease of cloning was generated by polymerase chain reaction (95°, 7 min; 5 cycles at 95°, 1 min, 70°, 1 min, 72°, 2 min; followed by 15 cycles at 94°, 1 min, 56°, 1 min, 72°, 2.5 min; 72°, 5 min) and inserted into the Epstein-Barr virus-based expression vector pEBon via the Xho I and Hind III sites. In another construction, the above cDNA fragment with a blunt end at the 3' end was first subcloned into the cytomegalovirus-based expression vector pRK5 containing an epitope-tagged gD by deleting the Rse sequences from a gD-Rse construct in pRK5 (Mark et al., J. Biol. Chem., 269: 10720–10728 [1994]) via the Sal I and EcoR V sites and inserting the SMDF sequences. Epitope-tagged gD-Rse was constructed by fusing the coding sequences for amino acids 1–53 of herpes simplex virus type 1 glycoprotein D (Mark et al., supra) to the sequences encoding amino acids 41–890 of human Rse (Paborsky et al., Protein Eng., 3:547–553 [1990]). The resulting gD-SMDF insert was then subcloned into pEBon via the Hind III site. Orientation was determined by restriction digest and confirmed by sequencing. Plasmid DNA was purified on Qiagen columns. 293 cells (American Type Culture Collection, ATCC CRL 1573) were transfected with the SMDF/pEBon and gD-SMDF/pEBon expression vectors and the vector pEBon (as control) using a modified $CaPO_4$ mediated transfection protocol (Gorman, In DNA Cloning: A Practical Approach, Vol. II, D. M. Glover, ed. Washington, D.C.: IRL Press, pp 143–190 [1985]). After 4 days, transfected serum-free culture supernatants were assayed for SMDF expression in a kinase receptor activation (KIRA) ELISA (see Example 3 below). After 21 days, positive G418-resistant clones were expanded and confluent culture supernatants were analyzed for stimulation of receptor tyrosine phosphorylation by KIRA-ELISA and western blot.

EXAMPLE 3 erbB Receptor Activation

Biological activity of the SMDF cDNA transiently expressed in 293 cells using the pEBon vector system (as discussed in Example 2) was investigated. In view of the presence of an EGF-like domain in SMDF, unconcentrated (1×) and 10-fold concentrated (10×) culture supernatants were assayed for their ability to stimulate tyrosine phosphorylation in MCF-7 human breast tumor cell line overexpressing the p185$^{neu/HER2}$ by western blotting.

For the assay, MCF-7 breast tumor cells (ATCC HTB 26) grown in Dulbecco's minimum essential medium (50%)/F-12 (50%)/10% fetal bovine serum (Hyclone) to confluency in 24-well plates were transferred to medium without serum (assay medium) for 2 hrs. The cells were stimulated for 15 min at 37° with SMDF-transfected culture supernatants or recombinant HRGβ$_{177-244}$ (rHRGβ1, purified EGF-like domain of HRGβ1, residues 177–244, expressed in E. coli, Holmes et al., supra) diluted in assay medium containing 0.1% BSA, as indicated. The supernatants were aspirated and 100 µl of SDS sample buffer containing β-mercaptoethanol were added. The samples (15 µl) were heated and electrophoresed in a 4–20% polyacrylamide gel (Novex) and electroblotted onto a nitrocellulose membrane. The membranes were blocked with 5% bovine serum albumin in Tris-buffered saline containing 0.05% Tween-20 and incubated with an anti-phosphotyrosine monoclonal antibody (4G10, UBI) for 1 hr. at room temp. Bound anti-phosphotyrosine antibody was probed with an alkaline phosphatase-conjugated goat anti-mouse Immunoglobulin G antibody (Promega) for 30 min. at room temp. and visualized with 5-bromo-4-chloro-3-indoyl-1-phosphate and nitro-blue tetrazolium (Promega).

On western blot, a 185 kD protein in the stimulated MCF-7 cell lysate was detected by an anti-phosphotyrosine monoclonal antibody in cells treated with the SMDF-transfected culture supernatants and rHRGβ1$_{177-241}$ (Holmes et al., supra). The responses to different concentrations of rHRGβ1$_{177-241}$ (100 pM, 500 pM and 1 nM) and to the unconcentrated and 10× concentrated SMDF-transfected supernatants were both concentration-dependent. Cells treated with assay medium containing 0.1% BSA, serum-free transfection medium, or unconcentrated and 10-fold concentrated vector-transfected culture supernatants did not stimulate tyrosine phosphorylation of the 185 kD protein (which is most likely the erbB2/neu/HER2 receptor tyrosine kinase).

The tyrosine phosphorylation western blot assay described above was repeated using a rat skeletal muscle myoblast cell line (ATCC CRL 1769). It was found that SMDF-transfected culture supernatants (unconcentrated or 10× concentrated) could stimulate tyrosine phosphorylation of a 185 kD band in a concentration dependent manner. SMDF appeared to be more potent at stimulating phosphorylation of p185$^{HER2}$ than rHRG-β$_{177-244}$.

For the KIRA-ELISA, MCF-7 cells were plated at 2×10$^5$ cells/100 µl/well in microtiter plates and grown at 37° in 5% CO$_2$ overnight. The supernatants were decanted and cells were stimulated with SMDF-transfected culture supernatants (SMDF or gD-SMDF) or various concentrations (0–3000 pM) of rHRGβ1$_{177-244}$(rHRG-β1) for 30 min. at 37°. The supernatants were decanted and 100 µl of lysis buffer [50 mM HEPES, pH 7.5, 150 mM NaCL, 0.5% Triton X-100, 0.01% thimerosol, 30 KIU/ml aprotinin (ICN), 1 mM 4-(2-aminoethyl)-benzenesulfonyl fluoride hydrochloride (AEBSF, ICN), 2 mM sodium orthovanadate] was added to each well. The cells were then incubated with gentle shaking for 1 hr. at room temp. The cell lysates were transferred to wells (85 µl/well) and incubated for 2 hrs. at room temp. in an ELISA microtiter plate coated overnight at 4° C. with 100 µl/well of affinity-purified polyclonal rabbit anti-HER2 extracellular domain antibody (1 µg/ml in 50 mM Sodium carbonate, pH 9.6), blocked for 60 min. at room temp. with 150 µl of 0.5% BSA, 0.01% thimerosal in PBS, and washed 6 times with wash buffer (PBS containing 0.05% Tween-20 and 0.01% thimerosal). The plate was washed and incubated for 2 hrs. at room temp. with 100 µl of a biotinylated anti-phosphotyrosine antibody (4G10, UBI) diluted 1:2000 in dilution buffer (PBS containing 0.5% BSA, 0.05% Tween-20, 5 mM EDTA, 0.01% thimerosol). The plate was washed and incubated for 30 min. at room temp. in 100 µl of horseradish peroxidase-conjugated streptavidin (Zymed Laboratories) diluted 1:10000 in dilution buffer. After washing, 100 µl of freshly prepared substrate solution (tetramethyl benzidine, 2-component substrate kit, Kirkegaard and Perry) was added and the reaction was allowed to proceed for 10 min. before the addition of 100 µl 1.0 M H$_3$PO$_4$. The absorbance at 450 nm was determined with a reference wavelength of 650 nm (ABS$_{450/650}$) using a vmax reader (Molecular Devices). A reproducible standard curve was generated by parallel stimulation with known concentrations of rHRGβ1 and presented as pM β1 vs. mean ABS$_{450/650}$±SD. Assay results correlated closely with quantitative anti-phosphotyrosine western blot analysis. Sample concentrations were expressed as pM rHRGβ1 activity.

The SMDF-transfected cell supernatants show a range of KIRA-activity of 20–160pM relative to the activity of rHRGβ1.

Thus, unlike HRGβ3 and GGFHFB1 which were not released from COS-7 cells transfected with respective cDNA encoding them (see Holmes et al., supra and Marchionni et al., supra), SMDF appeared to be released from 293 cells transiently transfected with SMDF or gD-SMDF cDNA as suggested by the stimulation of tyrosine phosphorylation of a 185 kD protein by the two SMDF-transfected culture supernatants.

EXAMPLE 4

Generation of rat GGF Clones

The partial sequence of rat GGF cDNA (543 bp, equivalent to nt 964–1508 of human GGF clone BS4) was generated by polymerase chain reaction amplification of cDNA fragments prepared from rat brain polyA$^+$ RNA. Amplification reactions were performed using Taq DNA polymerase in a Perkin-Elmer Model 480 thermocycler for 10 cycles at 95°, 1 min, 80°, 2.5 min; followed by 25 cycles at 95°, 1 min, 72°, 2.5 min. Amplified DNA fragments were cloned at the Sma I site in pBluescript SK(–). Recombinants were identified and sequenced. The partial rat GGF sequence shares 90.2% identity with the human GGF sequence.

EXAMPLE 5

Northern Blot Analysis

Since SMDF shares a β-type EGF-like domain with some other neuregulins, a $^{32}$P-labeled cDNA fragment corresponding to the human SMDF cDNA 5' to the EGF-like sequence was used in northern blot analysis.

Total RNA was extracted from tissues or cells by the method of Chomczynski and Sacchi (*Anal. Biochem.*, 162:156–159 [1987]). PolyA⁺ RNA was isolated from total RNA on oligo(dT)-cellulose columns (QIAGEN) according to manufacturer's suggested procedures. Ethanol precipitated polyA⁺ RNA was dissolved in 1×MOPS buffer, 50% formamide, 17.5% formaldehyde, heat-denatured at 95° for 5 min, and electrophoresed in 1.2% agarose gels containing 1.1% formaldehyde (Kroczek and Siebert, *Anal. Biochem.*, 184:90–95 [1990]). The fractionated polyA⁺ RNA was then capillary transferred onto nylon membranes (Hybond, Amersham). The RNA blot was UV fixed and baked at 80° for 2 hr and prehybridized with 5×SSC, 5×Denhardt's, 0.1% SDS, 100 µg/ml salmon sperm DNA at 65° for 4 hr. The blots containing 2 µg each of polyA⁺ RNA from fetal human tissues and adult human tissues were purchased from Clontech. The hybridization probes were generated by polymerase chain reaction amplification of the following cDNA fragments: human SMDF, nt 507–1211 (705 bp) of clone BS1; human GGF, nt 519–1059 (541 bp) of clone BS4. The DNA probes were labeled with both $\alpha$-$^{32}$P-dATP and -dCTP by random priming using a mixed population of hexamers (Promega) to a specific activity of 7.5–11×10⁸ cpm/µg. The RNA blot was hybridized in the same hybridization solution with 2×10⁶ cpm/ml of probe at 65° for 20 hr. The blot was washed several times with 0.1×SSC, 0.1% SDS at room temperature, and finally washed with the same solution at 65° for 10 min. The blots were exposed to Kodak XAR-2 films with intensifying screens at −80° for 5–7 days.

On northern blot of polyA⁺ RNA from human fetal brain, two transcripts of 2.5 and 8.5 kb were detected. No hybridization signal was detected on the same blot of polyA⁺ RNA from human fetal lung, liver, and kidney. On the other hand, when a $^{32}$P-labeled probe corresponding to the kringle and part of the Ig-like domain of human GGF cDNA (which was also 5' to the shared EGF-like sequence) was used on a similar blot, two transcripts of 1.3 and 4.4 kb were detected in all 4 of the above-mentioned tissues.

Accordingly, these experiments demonstrate that there is a distinct difference in tissue distribution between SMDF and some other neuregulin variants in that it appears to be nervous tissue specific. This agrees with the wide distribution of mRNA in various tissues and cells reported for some other variants (Holmes et al., supra; Wen et al. [1992], supra; Falls et al., supra; Orr-Urtreger et al., supra; and Meyer and Birchmeier, supra).

EXAMPLE 6

In Situ Hybridization

In situ hybridization experiments were performed on human, rat, and mouse embryos and adult mouse, and rat brain and spinal cord. The $^{33}$P-labeled RNA probes correspond to the unique N-terminal coding sequence of human SMDF and the Ig-like domain of human and rat GGF.

Hybridization probes were generated by polymerase chain reaction amplification of the following cDNA fragments 3' to an added T7 promotor sequence as templates for in vitro transcription with the T7 RNA polymerase (Promega): human SMDF, nt 507–1172 (666 bp) of BS1; human GGF, nt 782–1306 (525 bp) of clone BS4; rat GGF, nt 964–1306 (343 bp) of rat GGF clone (Example 4). Both in vitro transcribed antisense and sense RNA were labeled with $\gamma$-$^{33}$P-UTP with (5000 Ci/mmol, Amersham) as described (Melton et al., *Nucleic Acid Res.*, 12:7035–7070 [1984]). The DNA template was removed by incubation with 1U RNAase-free DNAase (Promega) at 37° for 15 min. RNA samples were extracted twice with phenol-chloroform using yeast tRNA (Sigma) as carrier and precipitated with 100% ethanol in the presence of 0.3M sodium acetate, rinsed with 70% ethanol, and taken up with 10 mM Tris, 1 mM EDTA, pH 7.4 at a concentration of ~4×10⁵ cpm/µl. Hybridizations were performed according to the method of Wilcox et al., *J. Clin. Invest.*, 82:1134–1143 (1988) as modified by Phillips et al., *Science*, 250:290–294 (1990). Frozen tissue sections of 10 µm thickness in sealed slide boxes were allowed to warm up to room temperature and fixed in 4% paraformaldehyde, 1% glutaraldehyde at 4° for 30 min. After 2 washes in 0.5×SSC, the sections were covered with hybridization buffer (20 mM Tris-HCL, pH 8, 5 mM EDTA, 0.1M NaCl, 1×Denhardt's, 10% dextran sulfate, 10 mM DTT, 50% formamide; 0.4 ml per slide) and incubated at 42° for 3 hrs. $^{33}$P-labeled RNA probes in hybridization buffer containing tRNA as carrier were then added directly into the hybridization buffer on the slides to a final concentration of 8×10⁶ cpm/ml, mixed by gentle pipeting, and incubated at 55° overnight in humidified tight-covered boxes. After 2 washes in 2×SSC solution containing 10 mM $\beta$-mercaptoethanol, 1 mM EDTA, the sections were treated with RNAase A solution (20 µg/ml in 10 mM Tris-HCl, pH 8, 0.5 M NaCl) at room temperature for 30 min. After 2 more washes in 2×SSC-$\beta$-mercaptoethanol-EDTA solution at room temperature the sections were washed with high stringency buffer (0.1×SSC, 10 mM $\beta$-mercaptoethanol, 1 mM EDTA) at 55° for 2 hrs. The sections were then washed 2 times with 0.5×SSC at room temperature and dehydrated briefly each in 50%, 70%, and 90% ethanol containing 0.3M ammonium acetate, air-dried and exposed to Hyperfilm $\beta$MAX (Amersham) and NTB2 emulsion (Kodak). After development, the emulsion-dipped slides were counter-stained with cresyl violet.

Using the human SMDF probe, SMDF mRNA is localized mainly in the spinal cord and brain in the human and a E13.5 mouse embryo. In the spinal cord the highest levels of mRNA are in the ventral horn motor neurons and very high levels are also seen in the sensory neurons in the dorsal root ganglia. Among motor neurons, the expression is concentrated in large cells (which are later myelinated). High levels of SMDF mRNA are maintained in the motor and sensory neurons in adult mouse spinal cord. In the E13.5 mouse brain, high levels are seen in the lateral ventricle and cerebellum. Other regions of the brain where SMDF mRNA is detected include the entorhino cortex, adjacent hippocampus, thalamus and accessory olfactory bulb. Motor neurons in the hypoglossal tongue and face, and sensory neurons in the nasal epithelia also express SMDF mRNA.

Using a human GGF probe, GGF mRNA is also seen in the brain and spinal cord of the human and E13.5 mouse embryo. However, except for a moderate level of expression in the lateral ventricle of the E13.5 mouse brain, the hybridization signals seen in the ventral motor neurons and dorsal root ganglia of both embryonic human and mouse spinal cords are very weak in comparison with the SMDF mRNA signals. In the case of the human embryo, the GGF signals can not be discerned from the unusually high nonspecific background. The signals in some other regions, including the medulla and entorhinal cortex of the mouse embryonic brain, are barely above background. There are no detectable signals in the adult mouse spinal cord nor other regions described above for the SMDF mRNA.

When a rat GGF probe is used, moderate hybridization signals are seen in a E15.5 rat embryo in the lateral ventricle of the brain and dorsal root ganglia of the spinal cord. The signals in the ventral spinal cord motor neurons are much weaker. These data are similar to those obtained by Orr-Urtreger et al., supra, with a mouse NDF Ig probe for the distribution of mouse NDF in the mouse embryonic brain and spinal cord. GGF mRNA is also detected in other embryonic rat tissues (e.g., kidney).

In some of the previously reported northern or in situ analyses of neuregulins, the hybridization probes used were inclusive of the EGF-like sequence shared by SMDF (Holmes et al., supra; Wen et al. [1992], supra; Marchionni et al., supra; Meyer and Birchmeier, supra). Therefore, the SMDF mRNA would have been co-localized with other neuregulins in these experiments, and the hybridization signals observed in some tissues or regions might actually represent the SMDF mRNA and not the particular neuregulin in question.

When hybridization probes are designed such that SMDF is represented by its entire unique N-terminal sequence while other neuregulins are represented by the Ig-like sequence of recombinant human GGFII (which shares 100% identity with the Ig-like domain of HRGα, β's and human NDF β2b, β3; 87% with rat NDF; and 70% with ARIA; at the nucleotide level) in northern blot and in situ analysis, a major difference in tissue distribution is revealed. While other neuregulins are wide-spread in human tissues including in this study the brain, heart, lung, liver, and kidney, and spinal cord, SMDF is only found in the brain and spinal cord. Thus SMDF appears to be neural-tissue specific. Of particular interest is the high expression of SMDF mRNA in the ventral cord motor neurons and dorsal root ganglia of embryonic and adult spinal cord in the in situ studies. Although when using a rat probe, moderate levels of GGF mRNA are detected in the E15.5 rat dorsal root ganglia, the levels are much less than those of SMDF mRNA, while the marker for GGF mRNA in the ventral spinal cord motor neurons is much weaker. The in situ distribution of rat GGF mRNA in the rat brain and spinal cord is similar to that reported by Orr-Urtreger et al. (supra) using a mouse NDF probe which includes a partial Ig-like domain. Using a similar Ig probe, ARIA mRNA is also detected in embryonic chick ventral horn motor neurons but not in dorsal root ganglia (Falls et al., supra).

The unique nervous tissue-specific expression of SMDF mRNA distinguishes itself from other neuregulins. Without being limited to any one theory, its distinctively higher expression in the motor neurons and sensory neurons in the developing human, mouse, and rat spinal cords in comparison with other neuregulins suggests an action at the developing neuromuscular junction and possible roles in motor and sensory neuron development. At the neuromuscular junction, specializations of three cell types constitute the synapse: the motor neuron (nerve terminal), muscle fiber, and Schwann cell (see review by Hall and Sanes, *Cell* 72/Neuron 10 (Suppl.): 99–121 [1993]). SMDF is preferentially expressed in large motor neurons whose axons are myelinated, consistent with an action of SMDF on pre-terminal Schwann cell (which forms myelin) proliferation. The expression of SMDF in the adult mouse spinal cord motor neurons suggests that it may also act at mature neuromuscular junctions via reinnervation of muscle fibers by motor neurons following nerve damage.

EXAMPLE 7

Stimulation of Schwann Cell Proliferation by SMDF

Rat Schwann cells isolated from the sciatic nerves of 2 day-old rats were purified free of contaminating fibroblasts and other cells (Brockes et al., *Brain Res.*, 165:105–118 [1979]), and grown in the presence of 3 nM rHRGβ1$_{177-241}$. The cells were confirmed as Schwann cells by antibody staining of the Schwann cell surface marker P75$^{NGFR}$. Confluent cultures were washed twice with phosphate buffered saline, trypsinized and plated at 3.7×10$^4$ cells/well in a 24-well plate in serum-free transfection medium supplemented with insulin, transferrin, and trace elements. Duplicate wells were treated with serum-free transfection medium only, or SMDF-transfected 293 culture supernatants (10-fold concentrated) diluted 1:1 in serum-free medium. Five days later, Schwann cells treated with SMDF-transfected culture supernatants were confluent while cells in serum-free medium only did not survive. Thus, SMDF could promote the proliferation of Schwann cells.

What is claimed is:

1. An isolated antibody that binds to the N-terminal domain of sensory and motor neuron derived factor (SMDF), wherein the SMDF is human SMDF as in SEQ ID NO: 2 or SMDF having the amino acid sequence of a native SMDF from a nonhuman mammal.

2. An isolated antibody that binds to the N-terminal domain of sensory and motor neuron derived factor (SMDF) in SEQ ID NO: 2.

3. A composition comprising the antibody of claim 2 and a pharmaceutically acceptable carrier.

4. The antibody of claim 2 wherein the antibody is a neutralizing antibody.

5. The antibody of claim 2 which is a monoclonal antibody.

6. The antibody of claim 2 which comprises nonhuman complementarity determining region (CDR) residues and human immunoglobulin residues.

7. The antibody of claim 2 which is human.

8. The antibody of claim 2 which is an antibody fragment comprising antigen-binding residues of an antibody.

9. The antibody fragment of claim 8 which is a F(ab')$_2$.

10. The antibody fragment of claim 8 which is a Fab.

11. The antibody of claim 2 which is conjugated with a detectable label.

12. The antibody of claim 2 which binds SMDF with an affinity of at least about $10^7$ L/mole.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1872 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GAATTCGGGA  CAGCCTCTCC  TGCCGCCGCT  GCTGCTGCCG  CCGCCGCCAC      50

CGCCGGCTGG  TCCTCCTTCT  GCTTTTACTT  CTCCTGCATG  ACAGTTGTTT     100

TCTTCATCTG  AGCAGACACC  AGCTTCAGAT  GCTCGAGGTG  AGAAACATGC     150

CTTTCAGTTT  GGGCTACTGG  TTTACTTAAT  TAATCAGCCG  GCAGCTCCGT     200
```

| | | | | |
|---|---|---|---|---|
|CGATCTATTT|TCGTCCCTGT|CCTCTTGACG|AGCCCGGGAT|GGTTTGGAGT 250|
|AGCATTTAAA|AGAACTAGAA|AAGTGGCCCA|GAAACAGCAG|CTTAAAGAAT 300|
|TATTACGATA|TACTTTGATT|TTGTAGTTGC|TAGGAGCTTT|TCTTCCCCCC 350|
|TTGCATCTTT|CTGAACTCTT|CTTGATTTTA|ATAATGGCCT|TGGACTTGGA 400|
|CGATTTATCG|ATTTCCCCCT|GTAAGATGCT|GTATCATTTG|GTTGGGGGGG 450|
|CCTCTGCGTG|GTAATGGACC|GTGAGAGCGG|CCAGGCCTTC|TTCTGGAGGT 500|
|GAGCCGATGG|AGATTTATTC|CCCAGACATG|TCTGAGGTCG|CCGCCGAGAG 550|
|GTCCTCCAGC|CCCTCCACTC|AGCTGAGTGC|AGACCCATCT|CTTGATGGGC 600|
|TTCCGGCAGC|AGAAGACATG|CCAGAGCCCC|AGACTGAAGA|TGGGAGAACC 650|
|CCTGGACTCG|TGGGCCTGGC|CGTGCCCTGC|TGTGCGTGCC|TAGAAGCTGA 700|
|GCGCCTGAGA|GGTTGCCTCA|ACTCAGAGAA|AATCTGCATT|GTCCCCATCC 750|
|TGGCTTGCCT|GGTCAGCCTC|TGCCTCTGCA|TCGCCGGCCT|CAAGTGGGTA 800|
|TTTGTGGACA|AGATCTTTGA|ATATGACTCT|CCTACTCACC|TTGACCCTGG 850|
|GGGGTTAGGC|CAGGACCCTA|TTATTTCTCT|GGACGCAACT|GCTGCCTCAG 900|
|CTGTGTGGGT|GTCGTCTGAG|GCATACACTT|CACCTGTCTC|TAGGGCTCAA 950|
|TCTGAAAGTG|AGGTTCAAGT|TACAGTGCAA|GGTGACAAGG|CTGTTGTCTC 1000|
|CTTTGAACCA|TCAGCGGCAC|CGACACCGAA|GAATCGTATT|TTTGCCTTTT 1050|
|CTTTCTTGCC|GTCCACTGCG|CCATCCTTCC|CTTCACCCAC|CCGGAACCCT 1100|
|GAGGTGAGAA|CGCCCAAGTC|AGCAACTCAG|CCACAAACAA|CAGAAACTAA 1150|
|TCTCCAAACT|GCTCCTAAAC|TTTCTACATC|TACATCCACC|ACTGGGACAA 1200|
|GCCATCTTGT|AAAATGTGCG|GAGAAGGAGA|AAACTTTCTG|TGTGAATGGA 1250|
|GGGGAGTGCT|TCATGGTGAA|AGACCTTTCA|AACCCCTCGA|GATACTTGTG 1300|
|CAAGTGCCCA|AATGAGTTTA|CTGGTGATCG|CTGCCAAAAC|TACGTAATGG 1350|
|CCAGCTTCTA|CAGTACGTCC|ACTCCCTTTC|TGTCTCTGCC|TGAATAGGAG 1400|
|CATGCTCAGT|TGGTGCTGCT|TTCTTGTTGC|TGCATCTCCC|CTCAGATTCC 1450|
|ACCTAGAGCT|AGATGTGTCT|TACCAGATCT|AATATTGACT|GCCTCTGCCT 1500|
|GTCGCATGAG|AACATTAACA|AAAGCAATTG|TATTACTTCC|TCTGTTCGCG 1550|
|ACTAGTTGGC|TCTGAGATAC|TAATAGGTGT|GTGAGGCTCC|GGATGTTTCT 1600|
|GGAATTGATA|TTGAATGATG|TGATACAAAT|TGATAGTCAA|TATCAAGCAG 1650|
|TGAAATATGA|TAATAAAGGC|ATTTCAAAGT|CTCACTTTTA|TTGATAAAAT 1700|
|AAAAATCATT|CTACTGAACA|GTCCATCTTC|TTTATACAAT|GACCACATCC 1750|
|TGAAAAGGGT|GTTGCTAAGC|TGTAACCGAT|ATGCACTTGA|AATGATGGTA 1800|
|AGTTAATTTT|GATTCAGAAT|GTGTTATTTG|TCACAAATAA|ACATAATAAA 1850|
|AGGAAAAAAA|AAACCCGAAT|TC 1872| | |

( 2 ) INFORMATION FOR SEQ ID NO:2:

( i ) SEQUENCE CHARACTERISTICS:
        ( A ) LENGTH: 296 amino acids
        ( B ) TYPE: amino acid
        ( D ) TOPOLOGY: linear ( x i ) SEQUENCE DESCRIPTION: SEQ ID NO:2:

Met Glu Ile Tyr Ser Pro Asp Met Ser Glu Val Ala Ala Glu Arg

-continued

| 1 | | | | 5 | | | | | 10 | | | | | 15 |
|---|---|---|---|---|---|---|---|---|---|---|---|---|---|---|
| Ser | Ser | Ser | Pro | Ser | Thr | Gln | Leu | Ser | Ala | Asp | Pro | Ser | Leu | Asp |
| | | | | 20 | | | | | 25 | | | | | 30 |
| Gly | Leu | Pro | Ala | Ala | Glu | Asp | Met | Pro | Glu | Pro | Gln | Thr | Glu | Asp |
| | | | | 35 | | | | | 40 | | | | | 45 |
| Gly | Arg | Thr | Pro | Gly | Leu | Val | Gly | Leu | Ala | Val | Pro | Cys | Cys | Ala |
| | | | | 50 | | | | | 55 | | | | | 60 |
| Cys | Leu | Glu | Ala | Glu | Arg | Leu | Arg | Gly | Cys | Leu | Asn | Ser | Glu | Lys |
| | | | | 65 | | | | | 70 | | | | | 75 |
| Ile | Cys | Ile | Val | Pro | Ile | Leu | Ala | Cys | Leu | Val | Ser | Leu | Cys | Leu |
| | | | | 80 | | | | | 85 | | | | | 90 |
| Cys | Ile | Ala | Gly | Leu | Lys | Trp | Val | Phe | Val | Asp | Lys | Ile | Phe | Glu |
| | | | | 95 | | | | | 100 | | | | | 105 |
| Tyr | Asp | Ser | Pro | Thr | His | Leu | Asp | Pro | Gly | Gly | Leu | Gly | Gln | Asp |
| | | | | 110 | | | | | 115 | | | | | 120 |
| Pro | Ile | Ile | Ser | Leu | Asp | Ala | Thr | Ala | Ala | Ser | Ala | Val | Trp | Val |
| | | | | 125 | | | | | 130 | | | | | 135 |
| Ser | Ser | Glu | Ala | Tyr | Thr | Ser | Pro | Val | Ser | Arg | Ala | Gln | Ser | Glu |
| | | | | 140 | | | | | 145 | | | | | 150 |
| Ser | Glu | Val | Gln | Val | Thr | Val | Gln | Gly | Asp | Lys | Ala | Val | Val | Ser |
| | | | | 155 | | | | | 160 | | | | | 165 |
| Phe | Glu | Pro | Ser | Ala | Ala | Pro | Thr | Pro | Lys | Asn | Arg | Ile | Phe | Ala |
| | | | | 170 | | | | | 175 | | | | | 180 |
| Phe | Ser | Phe | Leu | Pro | Ser | Thr | Ala | Pro | Ser | Phe | Pro | Ser | Pro | Thr |
| | | | | 185 | | | | | 190 | | | | | 195 |
| Arg | Asn | Pro | Glu | Val | Arg | Thr | Pro | Lys | Ser | Ala | Thr | Gln | Pro | Gln |
| | | | | 200 | | | | | 205 | | | | | 210 |
| Thr | Thr | Glu | Thr | Asn | Leu | Gln | Thr | Ala | Pro | Lys | Leu | Ser | Thr | Ser |
| | | | | 215 | | | | | 220 | | | | | 225 |
| Thr | Ser | Thr | Thr | Gly | Thr | Ser | His | Leu | Val | Lys | Cys | Ala | Glu | Lys |
| | | | | 230 | | | | | 235 | | | | | 240 |
| Glu | Lys | Thr | Phe | Cys | Val | Asn | Gly | Gly | Glu | Cys | Phe | Met | Val | Lys |
| | | | | 245 | | | | | 250 | | | | | 255 |
| Asp | Leu | Ser | Asn | Pro | Ser | Arg | Tyr | Leu | Cys | Lys | Cys | Pro | Asn | Glu |
| | | | | 260 | | | | | 265 | | | | | 270 |
| Phe | Thr | Gly | Asp | Arg | Cys | Gln | Asn | Tyr | Val | Met | Ala | Ser | Phe | Tyr |
| | | | | 275 | | | | | 280 | | | | | 285 |
| Ser | Thr | Ser | Thr | Pro | Phe | Leu | Ser | Leu | Pro | Glu | | | | |
| | | | | 290 | | | | | 295 | 296 | | | | |

( 2 ) INFORMATION FOR SEQ ID NO:3:

( i ) SEQUENCE CHARACTERISTICS:
        ( A ) LENGTH: 422 amino acids
        ( B ) TYPE: amino acid
        ( D ) TOPOLOGY: linear ( x i ) SEQUENCE DESCRIPTION: SEQ ID NO:3:

| Met | Arg | Trp | Arg | Arg | Ala | Pro | Arg | Arg | Ser | Gly | Arg | Pro | Gly | Pro |
|---|---|---|---|---|---|---|---|---|---|---|---|---|---|---|
| 1 | | | | 5 | | | | | 10 | | | | | 15 |
| Arg | Ala | Gln | Arg | Pro | Gly | Ser | Ala | Ala | Arg | Ser | Ser | Pro | Pro | Leu |
| | | | | 20 | | | | | 25 | | | | | 30 |
| Pro | Leu | Leu | Pro | Leu | Leu | Leu | Leu | Gly | Thr | Ala | Ala | Leu | Ala |
| | | | | 35 | | | | | 40 | | | | | 45 |
| Pro | Gly | Ala | Ala | Ala | Gly | Asn | Glu | Ala | Ala | Pro | Ala | Gly | Ala | Ser |
| | | | | 50 | | | | | 55 | | | | | 60 |

```
Val  Cys  Tyr  Ser  Ser  Pro  Pro  Ser  Val  Gly  Ser  Val  Gln  Glu  Leu
               65                  70                       75

Ala  Gln  Arg  Ala  Ala  Val  Val  Ile  Glu  Gly  Lys  Val  His  Pro  Gln
               80                  85                       90

Arg  Arg  Gln  Gln  Gly  Ala  Leu  Asp  Arg  Lys  Ala  Ala  Ala  Ala  Ala
               95                 100                      105

Gly  Glu  Ala  Gly  Ala  Trp  Gly  Gly  Asp  Arg  Glu  Pro  Pro  Ala  Ala
              110                 115                      120

Gly  Pro  Arg  Ala  Leu  Gly  Pro  Pro  Ala  Glu  Glu  Pro  Leu  Leu  Ala
              125                 130                      135

Ala  Asn  Gly  Thr  Val  Pro  Ser  Trp  Pro  Thr  Ala  Pro  Val  Pro  Ser
              140                 145                      150

Ala  Gly  Glu  Pro  Gly  Glu  Glu  Ala  Pro  Tyr  Leu  Val  Lys  Val  His
              155                 160                      165

Gln  Val  Trp  Ala  Val  Lys  Ala  Gly  Gly  Leu  Lys  Lys  Asp  Ser  Leu
              170                 175                      180

Leu  Thr  Val  Arg  Leu  Gly  Thr  Trp  Gly  His  Pro  Ala  Phe  Pro  Ser
              185                 190                      195

Cys  Gly  Arg  Leu  Lys  Glu  Asp  Ser  Arg  Tyr  Ile  Phe  Phe  Met  Glu
              200                 205                      210

Pro  Asp  Ala  Asn  Ser  Thr  Ser  Arg  Ala  Pro  Ala  Ala  Phe  Arg  Ala
              215                 220                      225

Ser  Phe  Pro  Pro  Leu  Glu  Thr  Gly  Arg  Asn  Leu  Lys  Lys  Glu  Val
              230                 235                      240

Ser  Arg  Val  Leu  Cys  Lys  Arg  Cys  Ala  Leu  Pro  Pro  Gln  Leu  Lys
              245                 250                      255

Glu  Met  Lys  Ser  Gln  Glu  Ser  Ala  Ala  Gly  Ser  Lys  Leu  Val  Leu
              260                 265                      270

Arg  Cys  Glu  Thr  Ser  Ser  Glu  Tyr  Ser  Ser  Leu  Arg  Phe  Lys  Trp
              275                 280                      285

Phe  Lys  Asn  Gly  Asn  Glu  Leu  Asn  Arg  Lys  Asn  Lys  Pro  Gln  Asn
              290                 295                      300

Ile  Lys  Ile  Gln  Lys  Lys  Pro  Gly  Lys  Ser  Glu  Leu  Arg  Ile  Asn
              305                 310                      315

Lys  Ala  Ser  Leu  Ala  Asp  Ser  Gly  Glu  Tyr  Met  Cys  Lys  Val  Ile
              320                 325                      330

Ser  Lys  Leu  Gly  Asn  Asp  Ser  Ala  Ser  Ala  Asn  Ile  Thr  Ile  Val
              335                 340                      345

Glu  Ser  Asn  Ala  Thr  Ser  Thr  Ser  Thr  Thr  Gly  Thr  Ser  His  Leu
              350                 355                      360

Val  Lys  Cys  Ala  Glu  Lys  Glu  Lys  Thr  Phe  Cys  Val  Asn  Gly  Gly
              365                 370                      375

Glu  Cys  Phe  Met  Val  Lys  Asp  Leu  Ser  Asn  Pro  Ser  Arg  Tyr  Leu
              380                 385                      390

Cys  Lys  Cys  Pro  Asn  Glu  Phe  Thr  Gly  Asp  Arg  Cys  Gln  Asn  Tyr
              395                 400                      405

Val  Met  Ala  Ser  Phe  Tyr  Ser  Thr  Ser  Thr  Pro  Phe  Leu  Ser  Leu
              410                 415                      420

Pro  Glu
     422
```

( 2 ) INFORMATION FOR SEQ ID NO:4:

( i ) SEQUENCE CHARACTERISTICS:

(A) LENGTH: 645 amino acids
(B) TYPE: amino acid
(D) TOPOLOGY: linear (xi) SEQUENCE DESCRIPTION: SEQ ID NO:4:

| | | | | | | | | | | | | | | |
|---|---|---|---|---|---|---|---|---|---|---|---|---|---|---|
| Met | Ser | Glu | Arg | Lys | Glu | Gly | Arg | Gly | Lys | Gly | Lys | Gly | Lys | Lys |
| 1 | | | | 5 | | | | | 10 | | | | | 15 |
| Lys | Glu | Arg | Gly | Ser | Gly | Lys | Lys | Pro | Glu | Ser | Ala | Ala | Gly | Ser |
| | | | | 20 | | | | | 25 | | | | | 30 |
| Gln | Ser | Pro | Ala | Leu | Pro | Pro | Gln | Leu | Lys | Glu | Met | Lys | Ser | Gln |
| | | | | 35 | | | | | 40 | | | | | 45 |
| Glu | Ser | Ala | Ala | Gly | Ser | Lys | Leu | Val | Leu | Arg | Cys | Glu | Thr | Ser |
| | | | | 50 | | | | | 55 | | | | | 60 |
| Ser | Glu | Tyr | Ser | Ser | Leu | Arg | Phe | Lys | Trp | Phe | Lys | Asn | Gly | Asn |
| | | | | 65 | | | | | 70 | | | | | 75 |
| Glu | Leu | Asn | Arg | Lys | Asn | Lys | Pro | Gln | Asn | Ile | Lys | Ile | Gln | Lys |
| | | | | 80 | | | | | 85 | | | | | 90 |
| Lys | Pro | Gly | Lys | Ser | Glu | Leu | Arg | Ile | Asn | Lys | Ala | Ser | Leu | Ala |
| | | | | 95 | | | | | 100 | | | | | 105 |
| Asp | Ser | Gly | Glu | Tyr | Met | Cys | Lys | Val | Ile | Ser | Lys | Leu | Gly | Asn |
| | | | | 110 | | | | | 115 | | | | | 120 |
| Asp | Ser | Ala | Ser | Ala | Asn | Ile | Thr | Ile | Val | Glu | Ser | Asn | Glu | Ile |
| | | | | 125 | | | | | 130 | | | | | 135 |
| Ile | Thr | Gly | Met | Pro | Ala | Ser | Thr | Glu | Gly | Ala | Tyr | Val | Ser | Ser |
| | | | | 140 | | | | | 145 | | | | | 150 |
| Glu | Ser | Pro | Ile | Arg | Ile | Ser | Val | Ser | Thr | Glu | Gly | Ala | Asn | Thr |
| | | | | 155 | | | | | 160 | | | | | 165 |
| Ser | Ser | Ser | Thr | Ser | Thr | Ser | Thr | Thr | Gly | Thr | Ser | His | Leu | Val |
| | | | | 170 | | | | | 175 | | | | | 180 |
| Lys | Cys | Ala | Glu | Lys | Glu | Lys | Thr | Phe | Cys | Val | Asn | Gly | Gly | Glu |
| | | | | 185 | | | | | 190 | | | | | 195 |
| Cys | Phe | Met | Val | Lys | Asp | Leu | Ser | Asn | Pro | Ser | Arg | Tyr | Leu | Cys |
| | | | | 200 | | | | | 205 | | | | | 210 |
| Lys | Cys | Pro | Asn | Glu | Phe | Thr | Gly | Asp | Arg | Cys | Gln | Asn | Tyr | Val |
| | | | | 215 | | | | | 220 | | | | | 225 |
| Met | Ala | Ser | Phe | Tyr | Lys | His | Leu | Gly | Ile | Glu | Phe | Met | Glu | Ala |
| | | | | 230 | | | | | 235 | | | | | 240 |
| Glu | Glu | Leu | Tyr | Gln | Lys | Arg | Val | Leu | Thr | Ile | Thr | Gly | Ile | Cys |
| | | | | 245 | | | | | 250 | | | | | 255 |
| Ile | Ala | Leu | Leu | Val | Val | Gly | Ile | Met | Cys | Val | Val | Ala | Tyr | Cys |
| | | | | 260 | | | | | 265 | | | | | 270 |
| Lys | Thr | Lys | Lys | Gln | Arg | Lys | Lys | Leu | His | Asp | Arg | Leu | Arg | Gln |
| | | | | 275 | | | | | 280 | | | | | 285 |
| Ser | Leu | Arg | Ser | Glu | Arg | Asn | Asn | Met | Met | Asn | Ile | Ala | Asn | Gly |
| | | | | 290 | | | | | 295 | | | | | 300 |
| Pro | His | His | Pro | Asn | Pro | Pro | Pro | Glu | Asn | Val | Gln | Leu | Val | Asn |
| | | | | 305 | | | | | 310 | | | | | 315 |
| Gln | Tyr | Val | Ser | Lys | Asn | Val | Ile | Ser | Ser | Glu | His | Ile | Val | Glu |
| | | | | 320 | | | | | 325 | | | | | 330 |
| Arg | Glu | Ala | Glu | Thr | Ser | Phe | Ser | Thr | Ser | His | Tyr | Thr | Ser | Thr |
| | | | | 335 | | | | | 340 | | | | | 345 |
| Ala | His | His | Ser | Thr | Thr | Val | Thr | Gln | Thr | Pro | Ser | His | Ser | Trp |
| | | | | 350 | | | | | 355 | | | | | 360 |
| Ser | Asn | Gly | His | Thr | Glu | Ser | Ile | Leu | Ser | Glu | Ser | His | Ser | Val |
| | | | | 365 | | | | | 370 | | | | | 375 |

```
Ile Val Met Ser Ser     Val Glu Asn Ser Arg     His Ser Ser Pro Thr
                380                     385                     390
Gly Gly Pro Arg Gly     Arg Leu Asn Gly Thr     Gly Gly Pro Arg Glu
                395                     400                     405
Cys Asn Ser Phe Leu     Arg His Ala Arg Glu     Thr Pro Asp Ser Tyr
                410                     415                     420
Arg Asp Ser Pro His     Ser Glu Arg Tyr Val     Ser Ala Met Thr Thr
                425                     430                     435
Pro Ala Arg Met Ser     Pro Val Asp Phe His     Thr Pro Ser Ser Pro
                440                     445                     450
Lys Ser Pro Pro Ser     Glu Met Ser Pro Pro     Val Ser Ser Met Thr
                455                     460                     465
Val Ser Met Pro Ser     Met Ala Val Ser Pro     Phe Met Glu Glu Glu
                470                     475                     480
Arg Pro Leu Leu Leu     Val Thr Pro Pro Arg     Leu Arg Glu Lys Lys
                485                     490                     495
Phe Asp His His Pro     Gln Gln Phe Ser Ser     Phe His His Asn Pro
                500                     505                     510
Ala His Asp Ser Asn     Ser Leu Pro Ala Ser     Pro Leu Arg Ile Val
                515                     520                     525
Glu Asp Glu Glu Tyr     Glu Thr Thr Gln Glu     Tyr Glu Pro Ala Gln
                530                     535                     540
Glu Pro Val Lys Lys     Leu Ala Asn Ser Arg     Arg Ala Lys Arg Thr
                545                     550                     555
Lys Pro Asn Gly His     Ile Ala Asn Arg Leu     Glu Val Asp Ser Asn
                560                     565                     570
Thr Ser Ser Gln Ser     Ser Asn Ser Glu Ser     Glu Thr Glu Asp Glu
                575                     580                     585
Arg Val Gly Glu Asp     Thr Pro Phe Leu Gly     Ile Gln Asn Pro Leu
                590                     595                     600
Ala Ala Ser Leu Glu     Ala Thr Pro Ala Phe     Arg Leu Ala Asp Ser
                605                     610                     615
Arg Thr Asn Pro Ala     Gly Arg Phe Ser Thr     Gln Glu Glu Ile Gln
                620                     625                     630
Ala Arg Leu Ser Ser     Val Ile Ala Asn Gln     Asp Pro Ile Ala Val
                635                     640                     645
```

( 2 ) INFORMATION FOR SEQ ID NO:5:

( i ) SEQUENCE CHARACTERISTICS:
        ( A ) LENGTH: 602 amino acids
        ( B ) TYPE: amino acid
        ( D ) TOPOLOGY: linear ( x i ) SEQUENCE DESCRIPTION: SEQ ID NO:5:

```
Met Trp Ala Thr Ser     Glu Gly Pro Leu Gln     Tyr Ser Leu Ala Pro
 1               5                      10                      15
Thr Gln Thr Asp Val     Asn Ser Ser Tyr Asn     Thr Val Pro Pro Lys
                20                      25                      30
Leu Lys Glu Met Lys     Asn Gln Glu Val Ala     Val Gly Gln Lys Leu
                35                      40                      45
Val Leu Arg Cys Glu     Thr Thr Ser Glu Tyr     Pro Ala Leu Arg Phe
                50                      55                      60
Lys Trp Leu Lys Asn     Gly Lys Glu Ile Thr     Lys Lys Asn Arg Pro
                65                      70                      75
```

-continued

| | | | | | | | | | | | | | | |
|---|---|---|---|---|---|---|---|---|---|---|---|---|---|---|
| Glu | Asn | Val | Lys | Ile 80 | Pro | Lys | Lys | Gln | Lys 85 | Lys | Tyr | Ser | Glu | Leu 90 |
| His | Ile | Tyr | Arg | Ala 95 | Thr | Leu | Ala | Asp | Ala 100 | Gly | Glu | Tyr | Ala | Cys 105 |
| Arg | Val | Ser | Ser | Lys 110 | Leu | Gly | Asn | Asp | Ser 115 | Thr | Lys | Ala | Ser | Val 120 |
| Ile | Ile | Thr | Asp | Thr 125 | Asn | Ala | Thr | Ser | Thr 130 | Ser | Thr | Thr | Gly | Thr 135 |
| Ser | His | Leu | Thr | Lys 140 | Cys | Asp | Ile | Lys | Gln 145 | Lys | Ala | Phe | Cys | Val 150 |
| Asn | Gly | Gly | Glu | Cys 155 | Tyr | Met | Val | Lys | Asp 160 | Leu | Pro | Asn | Pro | Pro 165 |
| Arg | Tyr | Leu | Cys | Arg 170 | Cys | Pro | Asn | Glu | Phe 175 | Thr | Gly | Asp | Arg | Cys 180 |
| Gln | Asn | Tyr | Val | Met 185 | Ala | Ser | Phe | Tyr | Lys 190 | His | Leu | Gly | Ile | Glu 195 |
| Phe | Met | Glu | Ala | Glu 200 | Glu | Leu | Tyr | Gln | Lys 205 | Arg | Val | Leu | Thr | Ile 210 |
| Thr | Gly | Ile | Cys | Ile 215 | Ala | Leu | Leu | Val | Val 220 | Gly | Ile | Met | Cys | Val 225 |
| Val | Ala | Tyr | Cys | Lys 230 | Thr | Lys | Lys | Gln | Arg 235 | Lys | Lys | Leu | His | Asp 240 |
| Arg | Leu | Arg | Gln | Ser 245 | Leu | Arg | Ser | Glu | Arg 250 | Asn | Asn | Val | Met | Asn 255 |
| Met | Ala | Asn | Gly | Pro 260 | His | His | Pro | Asn | Pro 265 | Pro | Pro | Asp | Asn | Val 270 |
| Gln | Leu | Val | Asn | Gln 275 | Tyr | Val | Ser | Lys | Asn 280 | Ile | Ile | Ser | Ser | Glu 285 |
| Arg | Val | Val | Glu | Arg 290 | Glu | Thr | Glu | Thr | Ser 295 | Phe | Ser | Thr | Ser | His 300 |
| Tyr | Thr | Ser | Thr | Thr 305 | His | His | Ser | Met | Thr 310 | Val | Thr | Gln | Thr | Pro 315 |
| Ser | His | Ser | Trp | Ser 320 | Asn | Gly | His | Thr | Glu 325 | Ser | Ile | Leu | Ser | Glu 330 |
| Ser | His | Ser | Val | Leu 335 | Val | Ser | Ser | Ser | Val 340 | Glu | Asn | Ser | Arg | His 345 |
| Thr | Ser | Pro | Thr | Gly 350 | Pro | Arg | Gly | Arg | Leu 355 | Asn | Gly | Ile | Gly | Gly 360 |
| Pro | Arg | Glu | Gly | Asn 365 | Ser | Phe | Leu | Arg | His 370 | Ala | Arg | Glu | Thr | Pro 375 |
| Asp | Ser | Tyr | Arg | Asp 380 | Ser | Pro | His | Ser | Glu 385 | Arg | Tyr | Val | Ser | Ala 390 |
| Met | Thr | Thr | Pro | Ala 395 | Arg | Met | Ser | Pro | Val 400 | Asp | Phe | His | Thr | Pro 405 |
| Thr | Ser | Pro | Lys | Ser 410 | Pro | Pro | Ser | Glu | Met 415 | Ser | Pro | Pro | Val | Ser 420 |
| Ser | Leu | Thr | Ile | Ser 425 | Ile | Pro | Ser | Val | Ala 430 | Val | Ser | Pro | Phe | Met 435 |
| Asp | Glu | Glu | Arg | Pro 440 | Leu | Leu | Leu | Val | Thr 445 | Pro | Pro | Arg | Leu | Arg 450 |
| Glu | Lys | Tyr | Asp | Asn 455 | His | Leu | Gln | Gln | Phe 460 | Asn | Ser | Phe | His | Asn 465 |
| Asn | Pro | Thr | His | Glu 470 | Ser | Asn | Ser | Leu | Pro 475 | Pro | Ser | Pro | Leu | Arg 480 |

```
Ile Val Glu Asp Glu Glu Tyr Glu Thr Thr Gln Glu Tyr Glu Pro
            485                 490                 495
Ala Gln Glu Pro Pro Lys Lys Leu Thr Asn Ser Arg Arg Val Lys
            500                 505                 510
Arg Thr Lys Pro Asn Gly His Ile Ser Ser Arg Val Glu Val Asp
            515                 520                 525
Ser Asp Thr Ser Ser Gln Ser Thr Ser Ser Glu Ser Glu Thr Glu
            530                 535                 540
Asp Glu Arg Ile Gly Glu Asp Thr Pro Phe Leu Ser Ile Gln Asn
            545                 550                 555
Pro Met Ala Thr Ser Leu Glu Pro Ala Ala Ala Tyr Arg Leu Ala
            560                 565                 570
Glu Asn Arg Thr Asn Pro Ala Asn Arg Phe Ser Thr Pro Glu Glu
            575                 580                 585
Leu Gln Ala Arg Leu Ser Ser Val Ile Ala Asn Gln Asp Pro Ile
            590                 595                 600
Ala Val
602
```